US009255254B2

(12) United States Patent
Valles et al.

(10) Patent No.: US 9,255,254 B2
(45) Date of Patent: Feb. 9, 2016

(54) *NYLANDERIA FULVA* VIRUS

(71) Applicant: The United States of America, as represented by the Secretary of Agriculture, Washington, DC (US)

(72) Inventors: Steven M. Valles, Gainesville, FL (US); David H. Oi, Gainesville, FL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/175,371

(22) Filed: Feb. 7, 2014

(65) Prior Publication Data

US 2014/0234262 A1    Aug. 21, 2014

Related U.S. Application Data

(60) Provisional application No. 61/762,529, filed on Feb. 8, 2013.

(51) Int. Cl.
| | | |
|---|---|---|
| *A01N 63/00* | (2006.01) | |
| *C12N 7/00* | (2006.01) | |
| *C07K 14/005* | (2006.01) | |

(52) U.S. Cl.
CPC ....... *C12N 7/00* (2013.01); *A01N 63/00* (2013.01); *C07K 14/005* (2013.01); *C12N 2770/00021* (2013.01); *C12N 2770/00031* (2013.01); *C12N 2770/32021* (2013.01)

(58) Field of Classification Search
CPC ............... A01N 63/00; C12N 2770/32021; C12N 7/00
USPC ............... 435/235.1; 530/350; 536/23.72
See application file for complete search history.

(56) References Cited

PUBLICATIONS

Calibeo, Dawn and Faith Oi, "Integrated Pest Management (IPM) of the CaribbeanCrazy Ant, Nylanderia (=Paratrechina) pubens (Forel)", (2011) University of Florida ENY-2006:1-4 http://edis.ifas.u#.edu.
Chen, Jian et al., "Defensive chemicals of tawny crazy ants, *Nylanderia fulva* (Hymenoptera: Formicidae) and their toxicity to red imported fire ants, *Solenopsis invicta* (Hymenoptera: Formicidae)", (2013) Toxicon 76:60-166.
Gorbalenya, Alexander, Eugene V. Koonin and Yuri I. Wolf, "A new superfamily of putative NTP-binding domains encoded by genomes of small DNA and RNA viruses", (1990) FEBS 262(1):145-148.
Gorbalenya, Alexander E. et al., "An NTP-Binding Motif Is the Most Conserved Sequence in a Highly Diverged Monophyletic Group of Proteins Involved in Positive Strand RNA Viral Replication" (1989) Journal of Molecular Evoution 28:256-268.
Gotzek, Dietrich et al., "The Importance of Using Multiple Approaches for Identifying Emerging Invasive Species: The Case of the Rasberry Crazy Ant in the United States", (2012) Plus One 7(9):1-10 (article No. e45314).
Hartley, C. J. et al, "Kelp Fly Virus: A Novel Group of Insect Picorna-Like Viruses as Defined by Genome Sequence Analysis and a Distinctive Virion Structure", (2005) Journal of Virology 79(21):13385-13398.
Lacey, L.A. et al., "Insect Pathogens as Biological Control Agents: Do They Have a Future?", (2001) Biological Control 21:230-248.
Lapolla, John S., Sean G. Brady and Steven O. Shattuck, "Phylogeny and taxonomy of the *Prenolepis* genus-group of ants (Hymenoptera: Formicidae)" (2010) Systematic Entomology 35:118-131.
Le Gall, Oliver et al., "Picornavirales, a proposed order of positive-sense single-stranded RNA viruses with a pseudo-T = 3 virion architecture", (2008) Archives of Virology 153:715-727.
Lebrun, Edward G., John Abbott and Lawrence E. Gilbert, "Imported crazy ant displaces imported fire ant, reduces and homogenizes grassland ant and arthropod assemblages", (2013) Biological Invasions 15(11):2429-2442.
Lebrun, Edward G. et al., "Chemical Warfare Among Invaders: A Detoxification Interaction Facilitates an Ant Invasion", (2014) Science 343(6174):1014-1017.
MacGown, J. and B. Layton, "The Invasive Rasberry Crazy Ant, *Nylanderia* sp. near pubens (Hymenoptera: Formicidae), Reported from Mississippi", (2010) Midsouth Entomologist 3:44-47 www.midsouthentomologist.org.msstate.edu.
Meyers, Jason Michael, "Identification, Distribution and Control of an Invasive Pest Ant, *Paratrechina* sp. (Hymenoptera: Formicidae), in Texas" (2008) Dissertation/Thesis Texas A&MU, 177 pages http://hdl.handle.net/1969.1/ETD-TAMU-2008-08-47.
Valles, Steven M. et al., "Metatranscriptomics and Pyrosequencing Facilitate Discovery of Potential Viral Natural Enemies of the Invasive Caribbean Crazy Ant, *Nylanderia pubens*", (2012) Plos One 7(2):1-9 (article No. e31828).
Valles, Steven M. and Yoshifumi Hashimoto, "Isolation and characterization of Solenopsis invicta virus 3, a new positive-strand RNA virus infecting the red imported fire ant, *Solenopsis invicta*" (2009) Virology 388:354-361.
Harlow, Erin, "Insect Spotlight: Caribbean Crazy Ant", (2011) Commercial Clippings Issue 13, p. 1 http://duval.ifas.ufkedu/documents/April-May2011CC.pdf.
Wetterer, James K. and Jozef L.W. Keularts, "Population Explosion of the hairy crazy ant, *Paratrechina pubens* (Hymenoptera: Formicidae), on St. Croix, US Virgin Islands", (2008) Florida Entomologist 91(3):423-427.

*Primary Examiner* — Janet Epps-Smith
(74) *Attorney, Agent, or Firm* — John D. Fado; David L. Marks; Lesley Shaw

(57) ABSTRACT

At least one novel virus capable of infecting crazy ants (*Nylanderia fulva*) is isolated, along with polynucleotide sequences and amino acid sequences of the virus. The virus is capable of be used as a biopesticide to control populations of crazy ants.

8 Claims, No Drawings

SEQUENCE LISTING

<160> NUMBER OF SEQ ID NOS: 97

<210> SEQ ID NO 1
<211> LENGTH: 1328
<212> TYPE: DNA
<213> ORGANISM: Nylanderia fulva virus

<400> SEQUENCE: 1

```
tcaccatatt ttcagacacc atggtttgat ttgttgaagg atagtgacgg aaaaccatta     60
ctgcctacga aactacctat ggaaaatgac attaccctac tgactgacga acagattgct    120
tccctttcta cggacaggga tggtaatcct tctgcacgtg taacgcaggc tttacaatgg    180
gcgcatttat tgcatgaacc agacctgaac ttctttgatg aagtttctca ggaatttatg    240
aaatatgtca acttaatcta cggcaagatg agtcttctta cagacgaaca agtcttacag    300
ggattcccaa agaaacatcc ctacgtagat tgtctaggtt cattgcagtt aaatgcttcc    360
attggatggt caatgaaggc tctgttcaac gttaacaaga aaaacgacat ctttactaag    420
gacgaggacg gactcattac gctcaacaac aatgacgcag caaaagcatt ttgggaaatg    480
ttccagaaag cgaaggaatt ggtgaacaat ggcgagccag tgcttgtaac agtagaggag    540
tgtggaaaga tggaaaaact caaagtttca aaataccaca ttggtcgcac tttttgtagt    600
atggactttc ttaatatctt gttagaacgc tacgtgatgg gctatttctc cgcaaaagcg    660
atgcgggacg atgattattg tgctgttggg atagatccct atgcgaattt tcatgacatg    720
tttgtggagc tgagaaaatt cgatcacgta tttgccatag attataaacg tttgacaaga    780
caattcccca atttttgata gatcttgtat ttgattgttt aattggtgtt aacaagaaaa    840
tggaaaaacc tctaaaatca atgaagaagt cttttcggca tagaattcaa atttcaggaa    900
attcattgtt tgagactata gggggaatgc cttctggctc atttataact gcgccactaa    960
attctgtatt taatttactt atcacctttg cagcatttgt ttatattttg aaactacatg   1020
gtattgatgc aacttgggag gatttccaga ggctcgttgt gtgcaggttc tatggggacg   1080
atggtgtgat tagtgtacat gaaagtatag caaaattttt caaccgcgta acgcttgcta   1140
aagcagtagc ccacttgttt ggcatgaata tgtcgtccgc taacaaagat gatgaactta   1200
aacctttcga cacttgggaa gaagtaaatt tcatttcacg ttattttcgg ttcctcaatg   1260
ggagaagtgt tgtgcttggt gctcttaaga aggaaacaat tctatcttat ttccacttca   1320
ctaagagc                                                            1328
```

<210> SEQ ID NO 2
<211> LENGTH: 570
<212> TYPE: DNA
<213> ORGANISM: Nylanderia fulva virus

<400> SEQUENCE: 2

```
gtagaaagat attcttggaa aggacccgga aacaatttat agcgcaatgc gaggcaattt     60
caaagaaact tcacttgtat atggagatcc ctccatacaa aatggctaac agtgccaccc    120
tctataatga gtggaaaatt accaacgtga agttgagact ttcagattga atgctccaaa    180
agagtatgcc aacactgtta ggtcgctctc ttctttgata gatgcatctt ccaacttgat    240
aactcaaatt gcctgcatgc agcataaatc acttccgcgc caggaacctg tagctgttct    300
gttcactgga actggaggaa ttggaaagac tcaggcgttg atgaacttgg cctacaaggt    360
taaggagaaa ttgtatccag gaatgacata tcacgaagca attggaacat acccaccaag    420
tcagaaatac tggcccaccc tgcatggaga gcctattggt atatatgatg aagtagcttc    480
```

```
ttgtacaacc tttgctgatg aacccttgct acgtgatatt aagtcaatag ttagtgcagt      540
ccatttcaac tgtgaaggtg cagcgctcac                                      570

<210> SEQ ID NO 3
<211> LENGTH: 1282
<212> TYPE: DNA
<213> ORGANISM: Nylanderia fulva virus

<400> SEQUENCE: 3
gcaggtatcg ctgtcttcag tcactccgat atcgccccag gactggtttt aagtccttca      60
aaatcctcaa ggaacaccat actggccata ccctttgagg gagttccttg aacactgccc     120
atacagtgaa taccaacaca tttgttctgg aattgtgagg agattgcgaa ataaggcaat     180
ccacaatctc caaatgatgt ataagcatga tttccttcca taactgccat ggcataatcc     240
gctttcactt tgtctgaggt cttgacactg gtagtgttga aatgagctgt catcttacca     300
acatgagcct gaacttggac ggtaacttta ttcaatgcct cgggaatacc aaaataccta     360
aagaattgta catgaaatga tcttgtagtc catctcccca tttctgccct agacggaaaa     420
tgttttgtaa tgtccgaaaa ttgaggtgct ttagaagaaa taatttcaca cattgctaaa     480
tctctgtttg ttccaacaaa tttattagtt actttgactt tatatttctt ttcgccaagc     540
tcatcacatc cgacatacca gtaccaatcc ttatggtctt taaatgaatg ggcaactgta     600
attaaagtac gggacttgac aaatattcca taattaactg ccttgaggtc ttcttgtgta     660
gtgtctccca ggtccgacat agacatatat acatgacaaa ggtttctatg aattacagga     720
tatataacat tattagatag ccgtgtgttg tcaaatctgg acataggttc ttggttatt      780 acagactgat cctgaagctc tggattgagc ttcttctgcc agagcaggca agtctcaaca     840
cgcataccta tctcatcagc ttgtgccata gcagcctgaa gttcttcgtt cgaatggttt     900
ggataacgtg cttgaagctg cgccaagcga gcgttccaag ccctaggatc gaagtgatcg     960
tcactatctt catcggtatt tgctttctta ctagcgcgca ctttcctcgc tcctttggca    1020
acctgctctt ccatttatc actcccgaaa gatttgacaa gcttatatac cacggcaata    1080
attcccgaca ccaaaaagat atataataag aagcgcacaa ttttgccttg aggtgtttcc    1140
aagaatagag aaaccttttc cttgacagct accgcacgtt gtactccttt ctcaaacaaa    1200
ttacctgaga cgttctgagt gagtctattg acaaattctt gtgtagcctt gagttgttga    1260
aattgattga caaaaatttc ag                                            1282

<210> SEQ ID NO 4
<211> LENGTH: 28
<212> TYPE: DNA
<213> ORGANISM: Artificial Sequence
<220> FEATURE:
<223> OTHER INFORMATION: Primer

<400> SEQUENCE: 4
ccctactgac tgacgaacag attgcttc                                        28

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
```
tgttgttgag cgtaatgagt ccgtcct                                          27

<210> SEQ ID NO 6
<211> LENGTH: 33
<212> TYPE: DNA
<213> ORGANISM: Artificial Sequence
<220> FEATURE:
<223> OTHER INFORMATION: Primer

<400> SEQUENCE: 6
acttcacttg tatatggaga tccctccata caa                                   33

<210> SEQ ID NO 7
<211> LENGTH: 32
<212> TYPE: DNA
<213> ORGANISM: Artificial Sequence
<220> FEATURE:
<223> OTHER INFORMATION: Primer

<400> SEQUENCE: 7
ttgcttcgtg atatgtcatt cctggataca at                                    32

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
tggtactggt atgtcggatg tgatgagct                                        29

<210> SEQ ID NO 9
<211> LENGTH: 31
<212> TYPE: DNA
<213> ORGANISM: Artificial Sequence
<220> FEATURE:
<223> OTHER INFORMATION: Primer

<400> SEQUENCE: 9
tgaggtcttg acactggtag tgttgaaagt a                                     31

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
ggccgtcatg gtggcgaata a                                                21

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
gaagcaatct gttcgtcagt cagtagggt                                        29

<210> SEQ ID NO 12
<211> LENGTH: 32
<212> TYPE: DNA
<213> ORGANISM: Artificial Sequence

```
<220> FEATURE:
<223> OTHER INFORMATION: Primer

<400> SEQUENCE: 12
tgtcattttc cataggtagt ttcgtaggca gt                                32

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
tccgtcacta tccttcaaca aatcaaacca                                   30

<210> SEQ ID NO 14
<211> LENGTH: 33
<212> TYPE: DNA
<213> ORGANISM: Artificial Sequence
<220> FEATURE:
<223> OTHER INFORMATION: Primer

<400> SEQUENCE: 14
aattcttgtg tagccttgag ttgttgaaat tga                               33

<210> SEQ ID NO 15
<211> LENGTH: 32
<212> TYPE: DNA
<213> ORGANISM: Artificial Sequence
<220> FEATURE:
<223> OTHER INFORMATION: Primer

<400> SEQUENCE: 15
ttctcaaaca aattacctga gacgttctga gt                                32

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
accttttcct tgacagctac cgcacgt                                      27

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17
agcatggtat tgaatttata gctcatgaag aat                               33

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18
attcttcatg agctataaat tcaataccat gct                               33
```

<210> SEQ ID NO 19
<211> LENGTH: 36
<212> TYPE: DNA
<213> ORGANISM: Artificial Sequence
<220> FEATURE:
<223> OTHER INFORMATION: Primer

<400> SEQUENCE: 19
aatcaggaaa ttggattact tgatcttttg gaatgt                                 36

<210> SEQ ID NO 20
<211> LENGTH: 39
<212> TYPE: DNA
<213> ORGANISM: Artificial Sequence
<220> FEATURE:
<223> OTHER INFORMATION: Primer

<400> SEQUENCE: 20
gtattcaaat tcattaagtt tccaaaggta atttcatgt                              39

<210> SEQ ID NO 21
<211> LENGTH: 32
<212> TYPE: DNA
<213> ORGANISM: Artificial Sequence
<220> FEATURE:
<223> OTHER INFORMATION: Primer

<400> SEQUENCE: 21
caattctatc ttatttccac ttcactaaga gc                                     32

<210> SEQ ID NO 22
<211> LENGTH: 32
<212> TYPE: DNA
<213> ORGANISM: Artificial Sequence
<220> FEATURE:
<223> OTHER INFORMATION: Primer

<400> SEQUENCE: 22
gctcttagtg aagtggaaat aagatagaat tg                                     32

<210> SEQ ID NO 23
<211> LENGTH: 26
<212> TYPE: DNA
<213> ORGANISM: Artificial Sequence
<220> FEATURE:
<223> OTHER INFORMATION: Primer

<400> SEQUENCE: 23
tcctcaatgg gagaagtgtt gtgctt                                            26

<210> SEQ ID NO 24
<211> LENGTH: 31
<212> TYPE: DNA
<213> ORGANISM: Artificial Sequence
<220> FEATURE:
<223> OTHER INFORMATION: Primer

<400> SEQUENCE: 24
tcgcaccatt catctttata tatgataacg c                                      31

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
atgccttctg gctcatttat aactgcgcca                                    30

<210> SEQ ID NO 26
<211> LENGTH: 29
<212> TYPE: DNA
<213> ORGANISM: Artificial Sequence
<220> FEATURE:
<223> OTHER INFORMATION: Primer

<400> SEQUENCE: 26
agcattgaga ttcccgattc agccgactt                                     29

<210> SEQ ID NO 27
<211> LENGTH: 29
<212> TYPE: DNA
<213> ORGANISM: Artificial Sequence
<220> FEATURE:
<223> OTHER INFORMATION: Primer

<400> SEQUENCE: 27
aagtcggctg aatcgggaat ctcaatgct                                     29

<210> SEQ ID NO 28
<211> LENGTH: 35
<212> TYPE: DNA
<213> ORGANISM: Artificial Sequence
<220> FEATURE:
<223> OTHER INFORMATION: Primer

<400> SEQUENCE: 28
aatcgagatt tataagttcc tctttcctcc taaca                              35

<210> SEQ ID NO 29
<211> LENGTH: 34
<212> TYPE: DNA
<213> ORGANISM: Artificial Sequence
<220> FEATURE:
<223> OTHER INFORMATION: Primer

<400> SEQUENCE: 29
aagagccaat atagcaaatt tgccaagatg agga                               34

<210> SEQ ID NO 30
<211> LENGTH: 36
<212> TYPE: DNA
<213> ORGANISM: Artificial Sequence
<220> FEATURE:
<223> OTHER INFORMATION: Primer

<400> SEQUENCE: 30
tcttagtgaa gtggaaataa gatagaattg tttcct                             36

<210> SEQ ID NO 31
<211> LENGTH: 34
<212> TYPE: DNA
<213> ORGANISM: Artificial Sequence
<220> FEATURE:
<223> OTHER INFORMATION: Primer

<400> SEQUENCE: 31
acgtttataa tctatggcaa atacgtgatc gaat                               34

<210> SEQ ID NO 32

```
<211> LENGTH: 32
<212> TYPE: DNA
<213> ORGANISM: Artificial Sequence
<220> FEATURE:
<223> OTHER INFORMATION: Primer

<400> SEQUENCE: 32
actgcctacg aaactaccta tggaaaatga ca                              32

<210> SEQ ID NO 33
<211> LENGTH: 38
<212> TYPE: DNA
<213> ORGANISM: Artificial Sequence
<220> FEATURE:
<223> OTHER INFORMATION: Primer

<400> SEQUENCE: 33
gtcttgtcaa acgtttataa tctatggcaa atacgtga                        38

<210> SEQ ID NO 34
<211> LENGTH: 38
<212> TYPE: DNA
<213> ORGANISM: Artificial Sequence
<220> FEATURE:
<223> OTHER INFORMATION: Primer

<400> SEQUENCE: 34
tcacgtattt gccatagatt ataaacgttt gacaagac                        38

<210> SEQ ID NO 35
<211> LENGTH: 36
<212> TYPE: DNA
<213> ORGANISM: Artificial Sequence
<220> FEATURE:
<223> OTHER INFORMATION: Primer

<400> SEQUENCE: 35
tcagctccac aaacatgtca tgaaaattcg catagg                          36

<210> SEQ ID NO 36
<211> LENGTH: 36
<212> TYPE: DNA
<213> ORGANISM: Artificial Sequence
<220> FEATURE:
<223> OTHER INFORMATION: Primer

<400> SEQUENCE: 36
cctatgcgaa ttttcatgac atgtttgtgg agctga                          36

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37
tatgcgtgtt gagacttgcc tgctctggca                                 30

<210> SEQ ID NO 38
<211> LENGTH: 37
<212> TYPE: DNA
<213> ORGANISM: Artificial Sequence
<220> FEATURE:
<223> OTHER INFORMATION: Primer

<400> SEQUENCE: 38
```
atgaatttga atacaactaa tcaaacctttt ttcgaca    37

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
acaggctatc atgggccctg gtaca    25

<210> SEQ ID NO 40
<211> LENGTH: 35
<212> TYPE: DNA
<213> ORGANISM: Artificial Sequence
<220> FEATURE:
<223> OTHER INFORMATION: Primer

<400> SEQUENCE: 40
agccacttca tgtattgttt atagatcatg tcctt    35

<210> SEQ ID NO 41
<211> LENGTH: 35
<212> TYPE: DNA
<213> ORGANISM: Artificial Sequence
<220> FEATURE:
<223> OTHER INFORMATION: Primer

<400> SEQUENCE: 41
aaggacatga tctataaaca atacatgaag tggct    35

<210> SEQ ID NO 42
<211> LENGTH: 35
<212> TYPE: DNA
<213> ORGANISM: Artificial Sequence
<220> FEATURE:
<223> OTHER INFORMATION: Primer

<400> SEQUENCE: 42
ggttcatata ctaccaaata gtccttccga ctatc    35

<210> SEQ ID NO 43
<211> LENGTH: 35
<212> TYPE: DNA
<213> ORGANISM: Artificial Sequence
<220> FEATURE:
<223> OTHER INFORMATION: Primer

<400> SEQUENCE: 43
gttataaaca gtttccatgg tgcatcacac ttatc    35

<210> SEQ ID NO 44
<211> LENGTH: 35
<212> TYPE: DNA
<213> ORGANISM: Artificial Sequence
<220> FEATURE:
<223> OTHER INFORMATION: Primer

<400> SEQUENCE: 44
acgggacttg acaaatattc cataattaac tgcct    35

<210> SEQ ID NO 45
<211> LENGTH: 35
<212> TYPE: DNA

<210> SEQ ID NO 45
<211> LENGTH: 35
<212> TYPE: DNA
<213> ORGANISM: Artificial Sequence
<220> FEATURE:
<223> OTHER INFORMATION: Primer

<400> SEQUENCE: 45
aggcagttaa ttatggaata tttgtcaagt cccgt                35

<210> SEQ ID NO 46
<211> LENGTH: 36
<212> TYPE: DNA
<213> ORGANISM: Artificial Sequence
<220> FEATURE:
<223> OTHER INFORMATION: Primer

<400> SEQUENCE: 46
tcctgagaaa cttcatcaaa gaagttcagg tctggt               36

<210> SEQ ID NO 47
<211> LENGTH: 36
<212> TYPE: DNA
<213> ORGANISM: Artificial Sequence
<220> FEATURE:
<223> OTHER INFORMATION: Primer

<400> SEQUENCE: 47
accagacctg aacttctttg atgaagtttc tcagga               36

<210> SEQ ID NO 48
<211> LENGTH: 35
<212> TYPE: DNA
<213> ORGANISM: Artificial Sequence
<220> FEATURE:
<223> OTHER INFORMATION: Primer

<400> SEQUENCE: 48
tgttaggtcg ctctcttctt tgatagatgc atctt                35

<210> SEQ ID NO 49
<211> LENGTH: 35
<212> TYPE: DNA
<213> ORGANISM: Artificial Sequence
<220> FEATURE:
<223> OTHER INFORMATION: Primer

<400> SEQUENCE: 49
aagatgcatc tatcaaagaa gagagcgacc taaca                35

<210> SEQ ID NO 50
<211> LENGTH: 30
<212> TYPE: DNA
<213> ORGANISM: Artificial Sequence
<220> FEATURE:
<223> OTHER INFORMATION: Primer

<400> SEQUENCE: 50
agatttatgc tgcatgcagg caatttgggt                      30

<210> SEQ ID NO 51
<211> LENGTH: 35
<212> TYPE: DNA
<213> ORGANISM: Artificial Sequence
<220> FEATURE:
<223> OTHER INFORMATION: Primer

<400> SEQUENCE: 51
tccagttcca gtgaacagaa ctgctacagg ttcct                35

<210> SEQ ID NO 52
<211> LENGTH: 31
<212> TYPE: DNA
<213> ORGANISM: Artificial Sequence
<220> FEATURE:
<223> OTHER INFORMATION: Primer

<400> SEQUENCE: 52
ttgtaagcca agttcatcaa cgcctgagtc t                           31

<210> SEQ ID NO 53
<211> LENGTH: 32
<212> TYPE: DNA
<213> ORGANISM: Artificial Sequence
<220> FEATURE:
<223> OTHER INFORMATION: Primer

<400> SEQUENCE: 53
aagaaggttt ggttggttgt attcaggttc at                          32

<210> SEQ ID NO 54
<211> LENGTH: 32
<212> TYPE: DNA
<213> ORGANISM: Artificial Sequence
<220> FEATURE:
<223> OTHER INFORMATION: Primer

<400> SEQUENCE: 54
taccctgctg ctagttgtgt accagggccc at                          32

<210> SEQ ID NO 55
<211> LENGTH: 31
<212> TYPE: DNA
<213> ORGANISM: Artificial Sequence
<220> FEATURE:
<223> OTHER INFORMATION: Primer

<400> SEQUENCE: 55
aagggtaacg ttcccaacaa gggtgagcaa t                           31

<210> SEQ ID NO 56
<211> LENGTH: 31
<212> TYPE: DNA
<213> ORGANISM: Artificial Sequence
<220> FEATURE:
<223> OTHER INFORMATION: Primer

<400> SEQUENCE: 56
attgctcacc cttgttggga acgttaccct t                           31

<210> SEQ ID NO 57
<211> LENGTH: 34
<212> TYPE: DNA
<213> ORGANISM: Artificial Sequence
<220> FEATURE:
<223> OTHER INFORMATION: Primer

<400> SEQUENCE: 57
caatctgtcg tagtgggatc aatgttcgta ccgt                        34

<210> SEQ ID NO 58
<211> LENGTH: 34
<212> TYPE: DNA
<213> ORGANISM: Artificial Sequence
<220> FEATURE:

```
<223> OTHER INFORMATION: Primer

<400> SEQUENCE: 58
attgaatcac tctggttgac tccttcaact ggct                                34

<210> SEQ ID NO 59
<211> LENGTH: 35
<212> TYPE: DNA
<213> ORGANISM: Artificial Sequence
<220> FEATURE:
<223> OTHER INFORMATION: Primer

<400> SEQUENCE: 59
aagagcacca agcacaacac ttctcccatt gagga                               35

<210> SEQ ID NO 60
<211> LENGTH: 35
<212> TYPE: DNA
<213> ORGANISM: Artificial Sequence
<220> FEATURE:
<223> OTHER INFORMATION: Primer

<400> SEQUENCE: 60
tcctcaatgg gagaagtgtt gtgcttggtg ctctt                               35

<210> SEQ ID NO 61
<211> LENGTH: 32
<212> TYPE: DNA
<213> ORGANISM: Artificial Sequence
<220> FEATURE:
<223> OTHER INFORMATION: Primer

<400> SEQUENCE: 61
aacttaaacc tttcgacact tgggaagaag ta                                  32

<210> SEQ ID NO 62
<211> LENGTH: 27
<212> TYPE: DNA
<213> ORGANISM: Artificial Sequence
<220> FEATURE:
<223> OTHER INFORMATION: Primer

<400> SEQUENCE: 62
agcgaaggag ttggtgaaca atggcga                                        27

<210> SEQ ID NO 63
<211> LENGTH: 28
<212> TYPE: DNA
<213> ORGANISM: Artificial Sequence
<220> FEATURE:
<223> OTHER INFORMATION: Primer

<400> SEQUENCE: 63
agaatgttct cgacccagtt tacggttg                                       28

<210> SEQ ID NO 64
<211> LENGTH: 28
<212> TYPE: DNA
<213> ORGANISM: Artificial Sequence
<220> FEATURE:
<223> OTHER INFORMATION: Primer

<400> SEQUENCE: 64
caaccgtaaa ctgggtcgag aacattct                                       28
```

```
<210> SEQ ID NO 65
<211> LENGTH: 31
<212> TYPE: DNA
<213> ORGANISM: Artificial Sequence
<220> FEATURE:
<223> OTHER INFORMATION: Primer

<400> SEQUENCE: 65
actcggacac tccctgatct gaatttctgg a                              31

<210> SEQ ID NO 66
<211> LENGTH: 31
<212> TYPE: DNA
<213> ORGANISM: Artificial Sequence
<220> FEATURE:
<223> OTHER INFORMATION: Primer

<400> SEQUENCE: 66
actttctcga ccatctctac attagtacgc a                              31

<210> SEQ ID NO 67
<211> LENGTH: 30
<212> TYPE: DNA
<213> ORGANISM: Artificial Sequence
<220> FEATURE:
<223> OTHER INFORMATION: Primer

<400> SEQUENCE: 67
agtgtaggcc atctattctc ttttgtcagt                                30

<210> SEQ ID NO 68
<211> LENGTH: 29
<212> TYPE: DNA
<213> ORGANISM: Artificial Sequence
<220> FEATURE:
<223> OTHER INFORMATION: Primer

<400> SEQUENCE: 68
tagggacata gtcaatttcc atcgcaagg                                 29

<210> SEQ ID NO 69
<211> LENGTH: 35
<212> TYPE: DNA
<213> ORGANISM: Artificial Sequence
<220> FEATURE:
<223> OTHER INFORMATION: Primer

<400> SEQUENCE: 69
actaagagcc ttgagccaca gcacctatct tcatt                          35

<210> SEQ ID NO 70
<211> LENGTH: 35
<212> TYPE: DNA
<213> ORGANISM: Artificial Sequence
<220> FEATURE:
<223> OTHER INFORMATION: Primer

<400> SEQUENCE: 70
tcttaagaag gaaacaattc tatcttactt ccact                          35

<210> SEQ ID NO 71
<211> LENGTH: 30
<212> TYPE: DNA
<213> ORGANISM: Artificial Sequence
<220> FEATURE:
<223> OTHER INFORMATION: Primer
```

<400> SEQUENCE: 71
actacgacag attgggccga agcagcaaat                                      30

<210> SEQ ID NO 72
<211> LENGTH: 31
<212> TYPE: DNA
<213> ORGANISM: Artificial Sequence
<220> FEATURE:
<223> OTHER INFORMATION: Primer

<400> SEQUENCE: 72
tgctgctcct ttacacatat caaagaaggt t                                    31

<210> SEQ ID NO 73
<211> LENGTH: 32
<212> TYPE: DNA
<213> ORGANISM: Artificial Sequence
<220> FEATURE:
<223> OTHER INFORMATION: Primer

<400> SEQUENCE: 73
tcaacagaac cttttctcat gtaccaaaat ca                                   32

<210> SEQ ID NO 74
<211> LENGTH: 30
<212> TYPE: DNA
<213> ORGANISM: Artificial Sequence
<220> FEATURE:
<223> OTHER INFORMATION: Primer

<400> SEQUENCE: 74
atgttctcga cccagtttac ggttggcggt                                      30

<210> SEQ ID NO 75
<211> LENGTH: 34
<212> TYPE: DNA
<213> ORGANISM: Artificial Sequence
<220> FEATURE:
<223> OTHER INFORMATION: Primer

<400> SEQUENCE: 75
ttgtggttca accactttct cgaccatctc taca                                 34

<210> SEQ ID NO 76
<211> LENGTH: 35
<212> TYPE: DNA
<213> ORGANISM: Artificial Sequence
<220> FEATURE:
<223> OTHER INFORMATION: Primer

<400> SEQUENCE: 76
tggaatagca ttgacacaaa tgatataatc gcaga                                35

<210> SEQ ID NO 77
<211> LENGTH: 32
<212> TYPE: DNA
<213> ORGANISM: Artificial Sequence
<220> FEATURE:
<223> OTHER INFORMATION: Primer

<400> SEQUENCE: 77
tcatcaacct tttcatcagt caacaattcg ga                                   32

<210> SEQ ID NO 78
<211> LENGTH: 34

<210> SEQ ID NO 78
<211> LENGTH: 34
<212> TYPE: DNA
<213> ORGANISM: Artificial Sequence
<220> FEATURE:
<223> OTHER INFORMATION: Primer

<400> SEQUENCE: 78
atctactaca agctgtgcct catttactga agga                           34

<210> SEQ ID NO 79
<211> LENGTH: 27
<212> TYPE: DNA
<213> ORGANISM: Artificial Sequence
<220> FEATURE:
<223> OTHER INFORMATION: Primer

<400> SEQUENCE: 79
aagaagggac ggagggtcgc cgttgaa                                   27

<210> SEQ ID NO 80
<211> LENGTH: 34
<212> TYPE: DNA
<213> ORGANISM: Artificial Sequence
<220> FEATURE:
<223> OTHER INFORMATION: Primer

<400> SEQUENCE: 80
tgtaggccat ctattctctt ttgtcagttt agta                           34

<210> SEQ ID NO 81
<211> LENGTH: 33
<212> TYPE: DNA
<213> ORGANISM: Artificial Sequence
<220> FEATURE:
<223> OTHER INFORMATION: Priner

<400> SEQUENCE: 81
actcaagctt caaattctgg caccaggtct gga                            33

<210> SEQ ID NO 82
<211> LENGTH: 31
<212> TYPE: DNA
<213> ORGANISM: Artificial Sequence
<220> FEATURE:
<223> OTHER INFORMATION: Primer

<400> SEQUENCE: 82
attacacgtg tatgtgtatg tgtgtgtgta t                              31

<210> SEQ ID NO 83
<211> LENGTH: 37
<212> TYPE: DNA
<213> ORGANISM: Artificial Sequence
<220> FEATURE:
<223> OTHER INFORMATION: Primer

<400> SEQUENCE: 83
acattgcaaa ataatgttta tttatcaagg ataatat                        37

<210> SEQ ID NO 84
<211> LENGTH: 34
<212> TYPE: DNA
<213> ORGANISM: Artificial Sequence
<220> FEATURE:
<223> OTHER INFORMATION: Primer

<400> SEQUENCE: 84
acgacgttat acgttctta tcggcatatt tact                                    34

<210> SEQ ID NO 85
<211> LENGTH: 32
<212> TYPE: DNA
<213> ORGANISM: Artificial Sequence
<220> FEATURE:
<223> OTHER INFORMATION: Primer

<400> SEQUENCE: 85
tatagacatc gtatttcgtt tgcttactat ca                                     32

<210> SEQ ID NO 86
<211> LENGTH: 34
<212> TYPE: DNA
<213> ORGANISM: Artificial Sequence
<220> FEATURE:
<223> OTHER INFORMATION: Primer

<400> SEQUENCE: 86
tactaaactg acaaaagaga atagatggcc taca                                   34

<210> SEQ ID NO 87
<211> LENGTH: 33
<212> TYPE: DNA
<213> ORGANISM: Artificial Sequence
<220> FEATURE:
<223> OTHER INFORMATION: Primer

<400> SEQUENCE: 87
tgaaattaaa gactttcctc gccttgcgat gga                                    33

<210> SEQ ID NO 88
<211> LENGTH: 33
<212> TYPE: DNA
<213> ORGANISM: Artificial Sequence
<220> FEATURE:
<223> OTHER INFORMATION: Primer

<400> SEQUENCE: 88
tgggaggact tgactattcc tatacgtgac gga                                    33

<210> SEQ ID NO 89
<211> LENGTH: 20
<212> TYPE: DNA
<213> ORGANISM: Artificial Sequence
<220> FEATURE:
<223> OTHER INFORMATION: Primer

<400> SEQUENCE: 89
ggccacgcgt cgactagtac                                                   20

<210> SEQ ID NO 90
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(36)
<223> OTHER INFORMATION: n is inosine

<400> SEQUENCE: 90
ggccasgcgt cgactagtac gggnngggnn gggnng                                 36

<210> SEQ ID NO 91
<211> LENGTH: 25
<212> TYPE: DNA
<213> ORGANISM: Artificial Sequence
<220> FEATURE:
<223> OTHER INFORMATION: Primer

<400> SEQUENCE: 91
gctgtcaacg atacgctacg taacg                                25

<210> SEQ ID NO 92
<211> LENGTH: 60
<212> TYPE: DNA
<213> ORGANISM: Artificial Sequence
<220> FEATURE:
<223> OTHER INFORMATION: Primer

<400> SEQUENCE: 92
gctgtcaacg atacgctacg taacggcatg acagtgtttt tttttttttt tttttttttt    60

<210> SEQ ID NO 93
<211> LENGTH: 7904
<212> TYPE: DNA
<213> ORGANISM: Nylanderia fulva virus
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1044)..(1044)
<223> OTHER INFORMATION: n is a, c, g, or t
<220> FEATURE:
<221> NAME/KEY: misc_feature
<222> LOCATION: (1212)..(1212)
<223> OTHER INFORMATION: n is a, c, g, or t
<220> FEATURE:
<221> NAME/KEY: misc_feature
<222> LOCATION: (3433)..(3433)
<223> OTHER INFORMATION: n is a, c, g, or t
<220> FEATURE:
<221> NAME/KEY: misc_feature
<222> LOCATION: (4167)..(4167)
<223> OTHER INFORMATION: n is a, c, g, or t
<220> FEATURE:
<221> NAME/KEY: misc_feature
<222> LOCATION: (4171)..(4171)
<223> OTHER INFORMATION: n is a, c, g, or t
<220> FEATURE:
<221> NAME/KEY: misc_feature
<222> LOCATION: (5634)..(5634)
<223> OTHER INFORMATION: n is a, c, g, or t

<400> SEQUENCE: 93
agaatgttct cgacccagtt tacggttggc ggtgtacgcc agaaatccag cagaactttg 60
gcctttttcc agaaattcag atcagggagt gtccgagtca ggaagtacat gcgtactaat 120
gtagagatgg tcgagaaagt ggttgaacca caaaacagcg agccagttga actggatgga 180
gtgaaccagg cgaatgaacc gatgtcggtc gttgatacgt tgatctctgc tgctgcagta 240
ctcataggca ttccattgtc aacagcttgc acaatctctt caatgttggt gaatatttcg 300
atgttattat gggaatttct gacagataaa acctcaatca aaattaaaat tgctttagga 360
tctgcgatta tatcatttgt gtcaatgcta ttccaacttt ttgattatga accaactgaa 420
aacgaaatta gtgatgtaaa aacacaattt tccgaattgt tgactgatga aaaggttgat 480
gaattggatg gaatagttgc atttcaagag atgtgcttaa aggctagata ttcaccagat 540 aaaaattcaga aattgtattc atccttcaag gttcgcaaaa atgttcctta ttgtcttcct 600

-continued

```
tcagtaaatg aggcacagct tgtagtagat tcaaaatttt ggactaaaga attcatcatc    660
ttctatcttg gcttaacaga aaatttgtac aacattttga aggctaatcc gcaacccgca    720
cctgaaaata cctttacgtg ggagggagct gaagaatata gcggagaaga tcctcctatt    780
gacttacaaa ctcaaatgga tcaattccaa attgttactg ttccatcaga tgggaattgt    840 atgtttggt caatgctggc ttcagatgcg aaggaactga caatgacgaa cttaaaaaca    900
ctcaaggact ccttcaatgc tctttccctc acgaaagagg agatgcagat tgtgaacacc    960
tatggtgcgt ggggcacttc tgatatgcta tttaaatggt gcacccanta tagacgctca   1020
ttatatcttg ctcaaatgaa caangaagga attggccata ctgtttattt tgatggagga   1080
atgcggaaga cgggtcctcc ccttaagatc atatattacc ctatacaaga acacttcaat   1140
gccttcattg agaaaaaggg taacgttccc aacaagggtg agcaatggta caacggtacg   1200
aacattgatc cnactacgac agattgggcc gaagcagcaa ataagcaaga tgagcagaag   1260
ccagttgaag gagtcaacca gagtgattca atgaaggata aatttacgga tttagcagtt   1320 gaaattttg acaaaatatt tggcttactt ttcggaataa tttatatcaa aaccactaaa   1380
actaatgcac cattgcgaga tctagccaca tccttttccc ttggaaaact tctgaaagaa   1440
ggagctgttg acacaaaggc tgcagtgaaa aagatatttc tggaaaagga cccggaaaag   1500
caatttatag cgcaatgcga ggcaatttca aagaagcttc acttgtatat ggagatccct   1560
ccatacaaaa tggcaaacag cgccaccctc tacaacgagt ggaaaaatta ccagcgtgaa   1620
gtcgagactt tcagattgaa tgctccaaaa gagtatgcca atactgttag gtcgctctct   1680
tctttgatag atgcatcttc caacttaata acccaaattg cctgcatgca gcataaatct   1740
cttccacgcc aggaacctgt agcagttctg ttcactggaa ctggaggaat tggaaagact   1800
caggcgttga tgaacttggc ttacaaggtt aaggagaaat tgtatccagg aatgacatat   1860
cacgaagcaa ttgaacata cccaccaagc cagaagtact ggcccactct gcatggagag   1920
cctatcggta tatatgatga agtagcttct tgtacaacct tgctgatga acccttgcta   1980 cgtgatatta agtcaatagt tagtgcagtc catttcaact gtgaaggcgc agctctgtcc   2040
cagaagcaaa atccgatgca gcagcacctc atctgcatgt cctcaaatca aacccttgag   2100
ggcctgcaga agatggctag cgatcagttc gataaatctt ctgttccatc cttctggcga   2160
agaatccaaa cttacgaatg cgctagacca gacaatatgc cacctttcga tcctaataat   2220
ccccaacctg gagattttag aaaagattat agtcatattt acttcaataa gcacgttttc   2280
gatgtaaaaa ctggaacaac tagatttctt caaagattaa ctatggatga ggtcattgcg   2340
gacaccgttt cgagaattca aaccaaaaag aataggcatc aagttgaaat ggacaaacta   2400
ctttctgaga ctgcaatttc cggagtcaat caatcggact ctgctgatca ctttgttgta   2460
aatatcaatg ggcgtgcagc agctggaaag tcgcgcctgc ttgaggcagc tgtttctgat   2520
tttgttaagg tgttaaatta ccaagttgta aggtattgcg accttgagaa gatggcaggc   2580
ggaaaacgtt tgaagaaaag ggtaattcta atagtagatg acgatatttt cctcaattct   2640
ccagaaattg agcaaaaata tatgcattgc tacaataaca tcctagcaaa tggatcagtc   2700
atctttgtgg ccacaaatat ctcacctggc tactctagga ttccagtcat tggaactaat   2760
gggtataaaa ttattagaac ttcccctttc atcaacgagg gaatggtacg tagaatgggt   2820
tacataggct cgtttgtgga tactggatcc tcaaagcatg gtattgaatt tatagctcat   2880
gaagaattgt atcatattcc aaaagatcaa gtaatccaat ttcctgattt tagtccaaaa   2940
catgaaatta cctttggaaa tctaatgaac ctgaatacaa ccaaccaaac cttctttgat   3000
```

```
atgtgtaaag gagcagcaaa atttgcaact tttacggcaa aacaggccat tatgggccct    3060
ggtacacaac tagcagcagg gtattcacca gccctcgctt tcaatatggc tagctacact    3120
agagctgatg caaaggacat gatctataaa caatacatga agtggcttga tagtcggaag    3180
gactatttgg tagtgtatga acccgttcct actgttgatt ggaatttcaa gattttcgcg    3240
aacagagctt gcgatgtgcg cctttctcat aactacctgg agatgattaa caatatcttt    3300
tacgatcctg taaaatttga taagtgtgat gcaccatgga aactgtttat aaccagggat    3360
gtgtttgatg cttgtatgaa agacaaaagt aaattctcta ttaacgtttc gaactttact    3420
gaagatgtaa ttntgaatgt agtacgcaag tatgtcgatg gtctaacagc tttgggtatt    3480
gaacccaagt tgttagccga tatcggtgac caaggcgttt acgcttttgt taatggaaag    3540
ttgcatgttc agaaagagcg agtcgttaat agatattgta cttttagcat aaaggatgat    3600
gaagtttggt ttgagatgcc taacagagtg attatgtgta agtggaatag catccttggt    3660
tatcataacg gagaacattc catccccata gaacataatt tgaacctgca agaaactgaa    3720
attttttgtca atcaattcca acaactcaag gctacacaag aatttgttaa taggctcacg    3780
cagaacgttt caggtaatct tttcgagaaa ggagtacaac gtgcagtagc tgtcaaggaa    3840
aaagtttctc tgttcttgga aacacctcaa ggtaaaattg tgcgcttctt attatatatc    3900
ttttggtgt cgggaattat tgccgtggta tataagcttg tcaaatcttt tgggaatgat    3960
aaaatggaag agcaggttgc caagggagcg aggaaagtgc gtgccagcaa gaaagcaaat    4020
actgacgaag atagtgacga ccacttcgat cctagggctt ggaacgctcg cttggcgcag    4080
cttcaagcac gttatccaaa ccattcgaac gaagaacttc aggctgctat ggcacaagct    4140
gatgagaaag gtatgcgtgt tgagacntgc ntgctctggc agaagaagct caatccagag    4200
cttcaggatc agtctgtaaa caaccaagaa cctatgtcca gatttgacaa cacacggcta    4260
tctaataatg ttatatatcc tgtaattcat agaaatcttt gtcatgtata tatgtctatg    4320
tcagacctgg gagacactac acaagaagac ctcaaggcag ttaattatgg aatatttgtc    4380
aagtcccgta ctttaattac agttgcccat tcatttaagg accataaaga ctggtactgg    4440
tatgtcggat gtgatgagct tggcgaaaag aaatataaag tcaaattaac taataaattt    4500
gttggaacaa acagagattt agcaatgtgt gaaattattt cttctaaagc accacaattt    4560
tcggacatta caaaacattt tccgtctaga gcagaaatgg gaagatggac cacaagatca    4620
ttccatgtac aattctttag atattttggc attcctgagg cactaaataa agtttctgtc    4680
caagtccagg ctcatgttgg taagatgaca gctcatttca atactaccag tgtcaagact    4740
tcagacaaag tgaaagctga ttatgccatg gcagttatgg aaggaaatca tgcctataca    4800
tcatttggag actgtggatt gccttatttc gcaatctcct cacaattcca gaacaaatgt    4860
gttggtattc actgtatggg cagtgttcaa ggaacccat caagggtat ggccagtatg    4920
gtgttcctcg aggattttga aggactcaag aaccagtcct ggggtgatat cggagtgact    4980
gaggacagcg atacctgcaa tatttgtgat accaacacaa gtgttactca ggattgtgga    5040
aatatcatca tatgggattc acttcacact tttccaaaaa tgtcatggca gaatcatgtg    5100
agatcgtacc tacgcatgtt taactcaacg cacgctgttg tgttcaccta taactgggga    5160
acactgtggg gtagtgtaaa gcaccaacat acgaagttct atgccgatca cacgcgctgg    5220
atggatgaca ccaaggaggg tgtgtatcca gcgcatgagg ttggactaga ccatcgtaca    5280
aaggatgaga taaccatagt gaagtttgag aatgtttcaa tggcaaccct gcaagagttc    5340
```

```
ctgcgcaatg atacgatcat agggtttaga ttcgacggtt tcgtgagact tcgaaatgac   5400
aacatactga ttacgaccga catctacgtg cactatgaga ctaacttcac aaatcaatca   5460
tgtgacatat ttagtaaggt aaatctgcca tcgggcgatt caggctatat tttaaccgag   5520
ctgatgccca tttatcgcgg ggctcagata aatttcttaa atggcaaact taacgacacc   5580
cctttcgacc aaattaagga caatgaaact gtaaaagtat ttggaacatt caanagaacc   5640
ttttctcatg taccaaaatc accatatttt cagacaccgt ggttcgattt gttgaaggat   5700
agtgacggaa aaccattatt gcctacgaag ttgcctatgg agaacgacat taccctactg   5760
actgacgaac agattgcttc tcttctaca gatagggatg gtaatccttc tgcacgtgta   5820
acgcaggctt tacaatgggc gcatttattg catgaaccag acctgaactt ctttgatgaa   5880
gtttctcagg aatttatgaa atatgtcaac ctaatctacg gtaagatgag tcttcttacg   5940
gatgaacaag tcctacaggg attcccaaag aaacatccct acgtagattg cctaggttca   6000
ttgcagttaa atgcttccat tggatggtca atgaaggccc tgttcaacgt taacaagaaa   6060
aacgacatct ttactaaaga cgaagacgga ctcattacgc tcaacaacaa tgacgcagca   6120
aaagcatttt gggaaatgtt tcagaaagcg aaggagttgg tgaacaatgg cgagccagtg   6180
cttgtaacag tagaggagtg tgggaagatg gaaaaactta agtttcaaa ataccacatt   6240 ggtcgcactt tttgtagtat ggacttcctt aatatcttgt tagaacgata cgtgatgggc   6300
tatttctccg caaaagcaat gcgggacgat gactattgtg ccgttgggat agaccccatat   6360 gcgaattttc acgacatgtt tgtggagctg agaaaattcg atcacgtatt tgccatagat   6420
tataaacgtt tcgataagac aattccccaa tttctgatag atcttgtttt tgattgttta   6480
attggtgtta ataagaaaat ggaaaaacct ctaaaatcaa tgaagaaatc ttttcggcat   6540
agaattcaaa tttcaggaaa ttcattgttt gaaactatag ggggaatgcc ttctggctca   6600
tttataactg cgccactaaa ttctgtattt aatttactta tcacctttgc ggcatttgtt   6660
tacattttga aactacatgg tattgatgca acttgggagg atttccagag gctcgttgtg   6720
tgtaggttct atggggacga cggtgtgatt agcgtgcatg aaagtatagc aaaattttc    6780 aaccgcgtaa cacttgctaa agcagtagcc catttgtttg gcatgaatat gtcgtcagct   6840
aacaaagatg atgaacttaa acctttcgac acttgggaag aagtaaattt catttcacgt   6900
tattttcggt tcctcaatgg gagaagtgtt gtgcttggtg ctcttaagaa ggaaacaatt   6960
ctatcttact tccactttac taagagcctt gagccacagc acctatcttc attgctagaa   7020
aaggcagcag aagaggctag tatctggggg gaagaatttt ataactatgt agaggattta   7080
attcgtacat gtatagactg ctgtccacca ctcagaaaac atcttgcttt acgaaccttt   7140
aatttaacaa ttttggattt agaacaaaac gtgaaatctt tggaaaatca ggagcatctt   7200
gagctcccgg ggggtcaatt gtatttgat ttgctgcgag agtattacct gccctcaaaa   7260
caattcaaag cgttgcgatt ggcgttaaat gatcagtcat tctttgatag cactatggaa   7320
ttctctagcg tttccctgct taatgaactt tttcagaagg gcacggtctc caggcctaag   7380
tatactgtgc gccttgcacc tagcggcgac atttcatggg aaacaacgtt acacctcacc   7440
tttcatgaag ataattctac gcggagtatt actacagtcg gtgttggacg aactaaaagc   7500
gagtccaaag agggagcgtc atttaatgca cttaaaatta ttggaaaggt ccctgccgta   7560
tttcttaatg gaagaaagaa ggattctgcg gagatcactg gagtgaacca gtctgacttg   7620
aatgtgtgtc ggttttgtgg aaattattat gacgagtctc gttatcctca ggggtgtccc   7680
tgtaataagg agaatcggcc taataatgcc gactactggg aggacttgac tattcctata   7740
```

```
cgtgacggag aacgacctat gacttaccgt gaaatcaaag actttcctcg ccttgcgatg   7800
gaaattgact atgtccctac taaactgaca aaagagaata gatggcctac actttttaaa   7860
aaaaaaaaaa aaaaaaaaaa aaaaaaaaaa aaaaaaaaaa aaaa                    7904

<210> SEQ ID NO 94
<211> LENGTH: 2619
<212> TYPE: PRT
<213> ORGANISM: Nylanderia fulva virus
<220> FEATURE:
<221> NAME/KEY: misc_feature
<222> LOCATION: (336)..(336)
<223> OTHER INFORMATION: Xaa can be any naturally occurring amino acid
<220> FEATURE:
<221> NAME/KEY: misc_feature
<222> LOCATION: (348)..(348)
<223> OTHER INFORMATION: Xaa can be any naturally occurring amino acid
<220> FEATURE:
<221> NAME/KEY: misc_feature
<222> LOCATION: (1145)..(1145)
<223> OTHER INFORMATION: Xaa can be any naturally occurring amino acid
<220> FEATURE:
<221> NAME/KEY: misc_feature
<222> LOCATION: (1391)..(1391)
<223> OTHER INFORMATION: Xaa can be any naturally occurring amino acid
<220> FEATURE:
<221> NAME/KEY: misc_feature
<222> LOCATION: (1878)..(1878)
<223> OTHER INFORMATION: Xaa can be any naturally occurring amino acid

<400> SEQUENCE: 94

Arg Met Phe Ser Thr Gln Phe Thr Val Gly Gly Val Arg Gln Lys Ser
1               5                   10                  15

Ser Arg Thr Leu Ala Phe Phe Gln Lys Phe Arg Ser Gly Ser Val Arg
            20                  25                  30

Val Arg Lys Tyr Met Arg Thr Asn Val Glu Met Val Glu Lys Val Val
        35                  40                  45

Glu Pro Gln Asn Ser Glu Pro Val Glu Leu Asp Gly Val Asn Gln Ala
    50                  55                  60

Asn Glu Pro Met Ser Val Val Asp Thr Leu Ile Ser Ala Ala Ala Val
65                  70                  75                  80

Leu Ile Gly Ile Pro Leu Ser Thr Ala Cys Thr Ile Ser Ser Met Leu
                85                  90                  95

Val Asn Ile Ser Met Leu Leu Trp Glu Phe Leu Thr Asp Lys Thr Ser
            100                 105                 110

Ile Lys Ile Lys Ile Ala Leu Gly Ser Ala Ile Ile Ser Phe Val Ser
        115                 120                 125

Met Leu Phe Gln Leu Phe Asp Tyr Glu Pro Thr Glu Asn Glu Ile Ser
    130                 135                 140

Asp Val Lys Thr Gln Phe Ser Glu Leu Leu Thr Asp Glu Lys Val Asp
145                 150                 155                 160

Glu Leu Asp Gly Ile Val Ala Phe Gln Glu Met Cys Leu Lys Ala Arg
                165                 170                 175

Tyr Ser Pro Asp Lys Ile Gln Lys Leu Tyr Ser Ser Phe Lys Val Arg
            180                 185                 190

Lys Asn Val Pro Tyr Cys Leu Pro Ser Val Asn Glu Ala Gln Leu Val
        195                 200                 205

Val Asp Ser Lys Phe Trp Thr Lys Glu Phe Ile Ile Phe Tyr Leu Gly
    210                 215                 220

Leu Thr Glu Asn Leu Tyr Asn Ile Leu Lys Ala Asn Pro Gln Pro Ala
225                 230                 235                 240
```

```
Pro Glu Asn Thr Phe Thr Trp Glu Gly Ala Glu Tyr Ser Gly Glu
            245                 250                 255

Asp Pro Pro Ile Asp Leu Gln Thr Gln Met Asp Gln Phe Gln Ile Val
        260                 265                 270

Thr Val Pro Ser Asp Gly Asn Cys Met Phe Trp Ser Met Leu Ala Ser
            275                 280                 285

Asp Ala Lys Glu Leu Thr Met Thr Asn Leu Lys Thr Leu Lys Asp Ser
        290                 295                 300

Phe Asn Ala Leu Ser Leu Thr Lys Glu Glu Met Gln Ile Val Asn Thr
305                 310                 315                 320

Tyr Gly Ala Trp Gly Thr Ser Asp Met Leu Phe Lys Trp Cys Thr Xaa
                325                 330                 335

Tyr Arg Arg Ser Leu Tyr Leu Ala Gln Met Asn Xaa Glu Gly Ile Gly
            340                 345                 350

His Thr Val Tyr Phe Asp Gly Met Arg Lys Thr Gly Pro Pro Leu
            355                 360                 365

Lys Ile Ile Tyr Tyr Pro Ile Gln Glu His Phe Asn Ala Phe Ile Glu
        370                 375                 380

Lys Lys Gly Asn Val Pro Asn Lys Gly Glu Gln Trp Tyr Asn Gly Thr
385                 390                 395                 400

Asn Ile Asp Pro Thr Thr Thr Asp Trp Ala Glu Ala Ala Asn Lys Gln
                405                 410                 415

Asp Glu Gln Lys Pro Val Glu Gly Val Asn Gln Ser Asp Ser Met Lys
            420                 425                 430

Asp Lys Phe Thr Asp Leu Ala Val Glu Ile Phe Asp Lys Ile Phe Gly
        435                 440                 445

Leu Leu Phe Gly Ile Ile Tyr Ile Lys Thr Thr Lys Thr Asn Ala Pro
450                 455                 460

Leu Arg Asp Leu Ala Thr Ser Phe Ser Leu Gly Lys Leu Leu Lys Glu
465                 470                 475                 480

Gly Ala Val Asp Thr Lys Ala Ala Val Glu Lys Ile Phe Leu Glu Lys
                485                 490                 495

Asp Pro Glu Lys Gln Phe Ile Ala Gln Cys Glu Ala Ile Ser Lys Lys
            500                 505                 510

Leu His Leu Tyr Met Glu Ile Pro Pro Tyr Lys Met Ala Asn Ser Ala
        515                 520                 525

Thr Leu Tyr Asn Glu Trp Lys Asn Tyr Gln Arg Glu Val Glu Thr Phe
    530                 535                 540

Arg Leu Asn Ala Pro Lys Glu Tyr Ala Asn Thr Val Arg Ser Leu Ser
545                 550                 555                 560

Ser Leu Ile Asp Ala Ser Ser Asn Leu Ile Thr Gln Ile Ala Cys Met
                565                 570                 575

Gln His Lys Ser Leu Pro Arg Gln Glu Pro Val Ala Val Leu Phe Thr
            580                 585                 590

Gly Thr Gly Gly Ile Gly Lys Thr Gln Ala Leu Met Asn Leu Ala Tyr
        595                 600                 605

Lys Val Lys Glu Lys Leu Tyr Pro Gly Met Thr Tyr His Glu Ala Ile
        610                 615                 620

Gly Thr Tyr Pro Pro Ser Gln Lys Tyr Trp Pro Thr Leu His Gly Glu
625                 630                 635                 640

Pro Ile Gly Ile Tyr Asp Glu Val Ala Ser Cys Thr Thr Phe Ala Asp
                645                 650                 655
```

-continued

Glu Pro Leu Leu Arg Asp Ile Lys Ser Ile Val Ser Ala Val His Phe
              660                 665                 670

Asn Cys Glu Gly Ala Ala Leu Ser Gln Lys Gln Asn Pro Met Gln Gln
         675                 680                 685

His Leu Ile Cys Met Ser Ser Asn Gln Thr Leu Glu Gly Leu Gln Lys
         690                 695                 700

Met Ala Ser Asp Gln Phe Asp Lys Ser Ser Val Pro Ser Phe Trp Arg
705                 710                 715                 720

Arg Ile Gln Thr Tyr Glu Cys Ala Arg Pro Asp Asn Met Pro Pro Phe
                 725                 730                 735

Asp Pro Asn Asn Pro Gln Pro Gly Asp Phe Arg Lys Asp Tyr Ser His
             740                 745                 750

Ile Tyr Phe Asn Lys His Val Phe Asp Val Lys Thr Gly Thr Thr Arg
         755                 760                 765

Phe Leu Gln Arg Leu Thr Met Asp Glu Val Ile Ala Asp Thr Val Ser
770                 775                 780

Arg Ile Gln Thr Lys Lys Asn Arg His Gln Val Glu Met Asp Lys Leu
785                 790                 795                 800

Leu Ser Glu Thr Ala Ile Ser Gly Val Asn Gln Ser Asp Ser Ala Asp
             805                 810                 815

His Phe Val Val Asn Ile Asn Gly Arg Ala Ala Ala Gly Lys Ser Arg
         820                 825                 830

Leu Leu Glu Ala Ala Val Ser Asp Phe Val Lys Val Leu Asn Tyr Gln
             835                 840                 845

Val Val Arg Tyr Cys Asp Leu Glu Lys Met Ala Gly Gly Lys Arg Leu
850                 855                 860

Lys Lys Arg Val Ile Leu Ile Val Asp Asp Ile Phe Leu Asn Ser
865                 870                 875                 880

Pro Glu Ile Glu Gln Lys Tyr Met His Cys Tyr Asn Asn Ile Leu Ala
             885                 890                 895

Asn Gly Ser Val Ile Phe Val Ala Thr Asn Ile Ser Pro Gly Tyr Ser
             900                 905                 910

Arg Ile Pro Val Ile Gly Thr Asn Gly Tyr Lys Ile Ile Arg Thr Ser
         915                 920                 925

Pro Phe Ile Asn Glu Gly Met Val Arg Arg Met Gly Tyr Ile Gly Ser
930                 935                 940

Phe Val Asp Thr Gly Ser Ser Lys His Gly Ile Glu Phe Ile Ala His
945                 950                 955                 960

Glu Glu Leu Tyr His Ile Pro Lys Asp Gln Val Ile Gln Phe Pro Asp
             965                 970                 975

Phe Ser Pro Lys His Glu Ile Thr Phe Gly Asn Leu Met Asn Leu Asn
         980                 985                 990

Thr Thr Asn Gln Thr Phe Phe Asp Met Cys Lys Gly Ala Ala Lys Phe
         995                 1000                1005

Ala Thr Phe Thr Ala Lys Gln Ala Ile Met Gly Pro Gly Thr Gln
         1010                1015                1020

Leu Ala Ala Gly Tyr Ser Pro Ala Leu Ala Phe Asn Met Ala Ser
         1025                1030                1035

Tyr Thr Arg Ala Asp Ala Lys Asp Met Ile Tyr Lys Gln Tyr Met
         1040                1045                1050

Lys Trp Leu Asp Ser Arg Lys Asp Tyr Leu Val Val Tyr Glu Pro
         1055                1060                1065

Val Pro Thr Val Asp Trp Asn Phe Lys Ile Phe Ala Asn Arg Ala

```
            1070                1075                1080
Cys Asp Val Arg Leu Ser His Asn Tyr Leu Glu Met Ile Asn Asn
    1085                1090                1095

Ile Phe Tyr Asp Pro Val Lys Phe Asp Lys Cys Asp Ala Pro Trp
    1100                1105                1110

Lys Leu Phe Ile Thr Arg Asp Val Phe Asp Ala Cys Met Lys Asp
    1115                1120                1125

Lys Ser Lys Phe Ser Ile Asn Val Ser Asn Phe Thr Glu Asp Val
    1130                1135                1140

Ile Xaa Asn Val Val Arg Lys Tyr Val Asp Gly Leu Thr Ala Leu
    1145                1150                1155

Gly Ile Glu Pro Lys Leu Leu Ala Asp Ile Gly Asp Gln Gly Val
    1160                1165                1170

Tyr Ala Phe Val Asn Gly Lys Leu His Val Gln Lys Glu Arg Val
    1175                1180                1185

Val Asn Arg Tyr Cys Thr Phe Ser Ile Lys Asp Asp Glu Val Trp
    1190                1195                1200

Phe Glu Met Pro Asn Arg Val Ile Met Cys Lys Trp Asn Ser Ile
    1205                1210                1215

Leu Gly Tyr His Asn Gly Glu His Ser Ile Pro Ile Glu His Asn
    1220                1225                1230

Leu Asn Leu Gln Glu Thr Glu Ile Phe Val Asn Gln Phe Gln Gln
    1235                1240                1245

Leu Lys Ala Thr Gln Glu Phe Val Asn Arg Leu Thr Gln Asn Val
    1250                1255                1260

Ser Gly Asn Leu Phe Glu Lys Gly Val Gln Arg Ala Val Ala Val
    1265                1270                1275

Lys Glu Lys Val Ser Leu Phe Leu Glu Thr Pro Gln Gly Lys Ile
    1280                1285                1290

Val Arg Phe Leu Leu Tyr Ile Phe Leu Val Ser Gly Ile Ile Ala
    1295                1300                1305

Val Val Tyr Lys Leu Val Lys Ser Phe Gly Asn Asp Lys Met Glu
    1310                1315                1320

Glu Gln Val Ala Lys Gly Ala Arg Lys Val Arg Ala Ser Lys Lys
    1325                1330                1335

Ala Asn Thr Asp Glu Asp Ser Asp Asp His Phe Asp Pro Arg Ala
    1340                1345                1350

Trp Asn Ala Arg Leu Ala Gln Leu Gln Ala Arg Tyr Pro Asn His
    1355                1360                1365

Ser Asn Glu Glu Leu Gln Ala Ala Met Ala Gln Ala Asp Glu Lys
    1370                1375                1380

Gly Met Arg Val Glu Thr Cys Xaa Leu Trp Gln Lys Lys Leu Asn
    1385                1390                1395

Pro Glu Leu Gln Asp Gln Ser Val Asn Asn Gln Glu Pro Met Ser
    1400                1405                1410

Arg Phe Asp Asn Thr Arg Leu Ser Asn Asn Val Ile Tyr Pro Val
    1415                1420                1425

Ile His Arg Asn Leu Cys His Val Tyr Met Ser Met Ser Asp Leu
    1430                1435                1440

Gly Asp Thr Thr Gln Glu Asp Leu Lys Ala Val Asn Tyr Gly Ile
    1445                1450                1455

Phe Val Lys Ser Arg Thr Leu Ile Thr Val Ala His Ser Phe Lys
    1460                1465                1470
```

-continued

```
Asp His Lys Asp Trp Tyr Trp Tyr Val Gly Cys Asp Glu Leu Gly
1475                1480                1485

Glu Lys Lys Tyr Lys Val Lys Leu Thr Asn Lys Phe Val Gly Thr
1490                1495                1500

Asn Arg Asp Leu Ala Met Cys Glu Ile Ile Ser Ser Lys Ala Pro
1505                1510                1515

Gln Phe Ser Asp Ile Thr Lys His Phe Pro Ser Arg Ala Glu Met
1520                1525                1530

Gly Arg Trp Thr Thr Arg Ser Phe His Val Gln Phe Phe Arg Tyr
1535                1540                1545

Phe Gly Ile Pro Glu Ala Leu Asn Lys Val Ser Val Gln Val Gln
1550                1555                1560

Ala His Val Gly Lys Met Thr Ala His Phe Asn Thr Thr Ser Val
1565                1570                1575

Lys Thr Ser Asp Lys Val Lys Ala Asp Tyr Ala Met Ala Val Met
1580                1585                1590

Glu Gly Asn His Ala Tyr Thr Ser Phe Gly Asp Cys Gly Leu Pro
1595                1600                1605

Tyr Phe Ala Ile Ser Ser Gln Phe Gln Asn Lys Cys Val Gly Ile
1610                1615                1620

His Cys Met Gly Ser Val Gln Gly Thr Pro Ser Lys Gly Met Ala
1625                1630                1635

Ser Met Val Phe Leu Glu Asp Phe Glu Gly Leu Lys Asn Gln Ser
1640                1645                1650

Trp Gly Asp Ile Gly Val Thr Glu Asp Ser Asp Thr Cys Asn Ile
1655                1660                1665

Cys Asp Thr Asn Thr Ser Val Thr Gln Asp Cys Gly Asn Ile Ile
1670                1675                1680

Ile Trp Asp Ser Leu His Thr Phe Pro Lys Met Ser Trp Gln Asn
1685                1690                1695

His Val Arg Ser Tyr Leu Arg Met Phe Asn Ser Thr His Ala Val
1700                1705                1710

Val Phe Thr Tyr Asn Trp Gly Thr Leu Trp Gly Ser Val Lys His
1715                1720                1725

Gln His Thr Lys Phe Tyr Ala Asp His Thr Arg Trp Met Asp Asp
1730                1735                1740

Thr Lys Glu Gly Val Tyr Pro Ala His Glu Val Gly Leu Asp His
1745                1750                1755

Arg Thr Lys Asp Glu Ile Thr Ile Val Lys Phe Glu Asn Val Ser
1760                1765                1770

Met Ala Thr Leu Gln Glu Phe Leu Arg Asn Asp Thr Ile Ile Gly
1775                1780                1785

Phe Arg Phe Asp Gly Phe Val Arg Leu Arg Asn Asp Asn Ile Leu
1790                1795                1800

Ile Thr Thr Asp Ile Tyr Val His Tyr Glu Thr Asn Phe Thr Asn
1805                1810                1815

Gln Ser Cys Asp Ile Phe Ser Lys Val Asn Leu Pro Ser Gly Asp
1820                1825                1830

Ser Gly Tyr Ile Leu Thr Glu Leu Met Pro Ile Tyr Arg Gly Ala
1835                1840                1845

Gln Ile Asn Phe Leu Asn Gly Lys Leu Asn Asp Thr Pro Phe Asp
1850                1855                1860
```

```
Gln Ile Lys Asp Asn Glu Thr Val Lys Val Phe Gly Thr Phe Xaa
1865                1870                1875

Arg Thr Phe Ser His Val Pro Lys Ser Pro Tyr Phe Gln Thr Pro
1880                1885                1890

Trp Phe Asp Leu Leu Lys Asp Ser Asp Gly Lys Pro Leu Leu Pro
1895                1900                1905

Thr Lys Leu Pro Met Glu Asn Asp Ile Thr Leu Leu Thr Asp Glu
1910                1915                1920

Gln Ile Ala Ser Leu Ser Thr Asp Arg Asp Gly Asn Pro Ser Ala
1925                1930                1935

Arg Val Thr Gln Ala Leu Gln Trp Ala His Leu His Glu Pro
1940                1945                1950

Asp Leu Asn Phe Phe Asp Glu Val Ser Gln Glu Phe Met Lys Tyr
1955                1960                1965

Val Asn Leu Ile Tyr Gly Lys Met Ser Leu Leu Thr Asp Glu Gln
1970                1975                1980

Val Leu Gln Gly Phe Pro Lys Lys His Pro Tyr Val Asp Cys Leu
1985                1990                1995

Gly Ser Leu Gln Leu Asn Ala Ser Ile Gly Trp Ser Met Lys Ala
2000                2005                2010

Leu Phe Asn Val Asn Lys Lys Asn Asp Ile Phe Thr Lys Asp Glu
2015                2020                2025

Asp Gly Leu Ile Thr Leu Asn Asn Asn Asp Ala Ala Lys Ala Phe
2030                2035                2040

Trp Glu Met Phe Gln Lys Ala Lys Glu Leu Val Asn Asn Gly Glu
2045                2050                2055

Pro Val Leu Val Thr Val Glu Glu Cys Gly Lys Met Glu Lys Leu
2060                2065                2070

Lys Val Ser Lys Tyr His Ile Gly Arg Thr Phe Cys Ser Met Asp
2075                2080                2085

Phe Leu Asn Ile Leu Leu Glu Arg Tyr Val Met Gly Tyr Phe Ser
2090                2095                2100

Ala Lys Ala Met Arg Asp Asp Asp Tyr Cys Ala Val Gly Ile Asp
2105                2110                2115

Pro Tyr Ala Asn Phe His Asp Met Phe Val Glu Leu Arg Lys Phe
2120                2125                2130

Asp His Val Phe Ala Ile Asp Tyr Lys Arg Phe Asp Lys Thr Ile
2135                2140                2145

Pro Gln Phe Leu Ile Asp Leu Val Phe Asp Cys Leu Ile Gly Val
2150                2155                2160

Asn Lys Lys Met Glu Lys Pro Leu Lys Ser Met Lys Lys Ser Phe
2165                2170                2175

Arg His Arg Ile Gln Ile Ser Gly Asn Ser Leu Phe Glu Thr Ile
2180                2185                2190

Gly Gly Met Pro Ser Gly Ser Phe Ile Thr Ala Pro Leu Asn Ser
2195                2200                2205

Val Phe Asn Leu Leu Ile Thr Phe Ala Ala Phe Val Tyr Ile Leu
2210                2215                2220

Lys Leu His Gly Ile Asp Ala Thr Trp Glu Asp Phe Gln Arg Leu
2225                2230                2235

Val Val Cys Arg Phe Tyr Gly Asp Asp Gly Val Ile Ser Val His
2240                2245                2250

Glu Ser Ile Ala Lys Phe Phe Asn Arg Val Thr Leu Ala Lys Ala
```

```
            2255                2260                2265

Val Ala His Leu Phe Gly Met Asn Met Ser Ser Ala Asn Lys Asp
    2270                2275                2280

Asp Glu Leu Lys Pro Phe Asp Thr Trp Glu Glu Val Asn Phe Ile
    2285                2290                2295

Ser Arg Tyr Phe Arg Phe Leu Asn Gly Arg Ser Val Val Leu Gly
    2300                2305                2310

Ala Leu Lys Lys Glu Thr Ile Leu Ser Tyr Phe His Phe Thr Lys
    2315                2320                2325

Ser Leu Glu Pro Gln His Leu Ser Ser Leu Leu Glu Lys Ala Ala
    2330                2335                2340

Glu Glu Ala Ser Ile Trp Gly Glu Phe Tyr Asn Tyr Val Glu
    2345                2350                2355

Asp Leu Ile Arg Thr Cys Ile Asp Cys Cys Pro Leu Arg Lys
    2360                2365                2370

His Leu Ala Leu Arg Thr Phe Asn Leu Thr Ile Leu Asp Leu Glu
    2375                2380                2385

Gln Asn Val Lys Ser Leu Glu Asn Gln Glu His Leu Glu Leu Pro
    2390                2395                2400

Gly Gly Gln Leu Tyr Phe Asp Leu Leu Arg Glu Tyr Tyr Leu Pro
    2405                2410                2415

Ser Lys Gln Phe Lys Ala Leu Arg Leu Ala Leu Asn Asp Gln Ser
    2420                2425                2430

Phe Phe Asp Ser Thr Met Glu Phe Ser Ser Val Ser Leu Leu Asn
    2435                2440                2445

Glu Leu Phe Gln Lys Gly Thr Val Ser Arg Pro Lys Tyr Thr Val
    2450                2455                2460

Arg Leu Ala Pro Ser Gly Asp Ile Ser Trp Glu Thr Thr Leu His
    2465                2470                2475

Leu Thr Phe His Glu Asp Asn Ser Thr Arg Ser Ile Thr Thr Val
    2480                2485                2490

Gly Val Gly Arg Thr Lys Ser Glu Ser Lys Glu Gly Ala Ser Phe
    2495                2500                2505

Asn Ala Leu Lys Ile Ile Gly Lys Val Pro Ala Val Phe Leu Asn
    2510                2515                2520

Gly Arg Lys Lys Asp Ser Ala Glu Ile Thr Gly Val Asn Gln Ser
    2525                2530                2535

Asp Leu Asn Val Cys Arg Phe Cys Gly Asn Tyr Tyr Asp Glu Ser
    2540                2545                2550

Arg Tyr Pro Gln Gly Cys Pro Cys Asn Lys Glu Asn Arg Pro Asn
    2555                2560                2565

Asn Ala Asp Tyr Trp Glu Asp Leu Thr Ile Pro Ile Arg Asp Gly
    2570                2575                2580

Glu Arg Pro Met Thr Tyr Arg Glu Ile Lys Asp Phe Pro Arg Leu
    2585                2590                2595

Ala Met Glu Ile Asp Tyr Val Pro Thr Lys Leu Thr Lys Glu Asn
    2600                2605                2610

Arg Trp Pro Thr Leu Phe
    2615

<210> SEQ ID NO 95
<211> LENGTH: 251
<212> TYPE: PRT
<213> ORGANISM: Nylanderia fulva virus
```

<400> SEQUENCE: 95

```
Gln Phe Ile Ala Gln Cys Glu Ala Ile Ser Lys Lys Leu His Leu Tyr
1               5                   10                  15
Met Glu Ile Pro Pro Tyr Lys Met Ala Asn Ser Ala Thr Leu Tyr Asn
            20                  25                  30
Glu Trp Lys Asn Tyr Gln Arg Glu Val Glu Thr Phe Arg Leu Asn Ala
        35                  40                  45
Pro Lys Glu Tyr Ala Asn Thr Val Arg Ser Leu Ser Leu Ile Asp
    50                  55                  60
Ala Ser Ser Asn Leu Ile Thr Gln Ile Ala Cys Met Gln His Lys Ser
65                  70                  75                  80
Leu Pro Arg Gln Glu Pro Val Ala Val Leu Phe Thr Gly Thr Gly Gly
                85                  90                  95
Ile Gly Lys Thr Gln Ala Leu Met Asn Leu Ala Tyr Lys Val Lys Glu
            100                 105                 110
Lys Leu Tyr Pro Gly Met Thr Tyr His Glu Ala Ile Gly Thr Tyr Pro
        115                 120                 125
Pro Ser Gln Lys Tyr Trp Pro Thr Leu His Gly Glu Pro Ile Gly Ile
    130                 135                 140
Tyr Asp Glu Val Ala Ser Cys Thr Thr Phe Ala Asp Glu Pro Leu Leu
145                 150                 155                 160
Arg Asp Ile Lys Ser Ile Val Ser Ala Val His Phe Asn Cys Glu Gly
                165                 170                 175
Ala Ala Leu Ser Gln Lys Gln Asn Pro Met Gln Gln His Leu Ile Cys
            180                 185                 190
Met Ser Ser Asn Gln Thr Leu Glu Gly Leu Gln Lys Met Ala Ser Asp
        195                 200                 205
Gln Phe Asp Lys Ser Ser Val Pro Ser Phe Trp Arg Arg Ile Gln Thr
    210                 215                 220
Tyr Glu Cys Ala Arg Pro Asp Asn Met Pro Pro Phe Asp Pro Asn Asn
225                 230                 235                 240
Pro Gln Pro Gly Asp Phe Arg Lys Asp Tyr Ser
                245                 250
```

<210> SEQ ID NO 96
<211> LENGTH: 201
<212> TYPE: PRT
<213> ORGANISM: Nylanderia fulva virus

<400> SEQUENCE: 96

```
Ser Leu Gln Leu Asn Ala Ser Ile Gly Trp Ser Met Lys Ala Leu Phe
1               5                   10                  15
Asn Val Asn Lys Lys Asn Asp Ile Phe Thr Lys Asp Glu Asp Gly Leu
            20                  25                  30
Ile Thr Leu Asn Asn Asn Asp Ala Ala Lys Ala Phe Trp Glu Met Phe
        35                  40                  45
Gln Lys Ala Lys Glu Leu Val Asn Asn Gly Glu Pro Val Leu Val Thr
    50                  55                  60
Val Glu Glu Cys Gly Lys Met Glu Lys Leu Lys Val Ser Lys Tyr His
65                  70                  75                  80
Ile Gly Arg Thr Phe Cys Ser Met Asp Phe Leu Asn Ile Leu Leu Glu
                85                  90                  95
Arg Tyr Val Met Gly Tyr Phe Ser Ala Lys Ala Met Arg Asp Asp Asp
            100                 105                 110
```

```
Tyr Cys Ala Val Gly Ile Asp Pro Tyr Ala Asn Phe His Asp Met Phe
        115                 120                 125

Val Glu Leu Arg Lys Phe Asp His Val Phe Ala Ile Asp Tyr Lys Arg
    130                 135                 140

Phe Asp Lys Thr Ile Pro Gln Phe Leu Ile Asp Leu Val Phe Asp Cys
145                 150                 155                 160

Leu Ile Gly Val Asn Lys Lys Met Glu Lys Pro Leu Lys Ser Met Lys
                165                 170                 175

Lys Ser Phe Arg His Arg Ile Gln Ile Ser Gly Asn Ser Leu Phe Glu
            180                 185                 190

Thr Ile Gly Gly Met Pro Ser Gly Ser
        195                 200
```

<210> SEQ ID NO 97
<211> LENGTH: 300
<212> TYPE: PRT
<213> ORGANISM: Nylanderia fulva virus

<400> SEQUENCE: 97

```
Ser Val His Glu Ser Ile Ala Lys Phe Phe Asn Arg Val Thr Leu Ala
1               5                   10                  15

Lys Ala Val Ala His Leu Phe Gly Met Asn Met Ser Ser Ala Asn Lys
                20                  25                  30

Asp Asp Glu Leu Lys Pro Phe Asp Thr Trp Glu Glu Val Asn Phe Ile
            35                  40                  45

Ser Arg Tyr Phe Arg Phe Leu Asn Gly Arg Ser Val Val Leu Gly Ala
        50                  55                  60

Leu Lys Lys Glu Thr Ile Leu Ser Tyr Phe His Phe Thr Lys Ser Leu
65                  70                  75                  80

Glu Pro Gln His Leu Ser Ser Leu Leu Glu Lys Ala Ala Glu Glu Ala
                85                  90                  95

Ser Ile Trp Gly Glu Glu Phe Tyr Asn Tyr Val Glu Asp Leu Ile Arg
            100                 105                 110

Thr Cys Ile Asp Cys Cys Pro Pro Leu Arg Lys His Leu Ala Leu Arg
        115                 120                 125

Thr Phe Asn Leu Thr Ile Leu Asp Leu Glu Gln Asn Val Lys Ser Leu
130                 135                 140

Glu Asn Gln Glu His Leu Glu Leu Pro Gly Gly Gln Leu Tyr Phe Asp
145                 150                 155                 160

Leu Leu Arg Glu Tyr Tyr Leu Pro Ser Lys Gln Phe Lys Ala Leu Arg
                165                 170                 175

Leu Ala Leu Asn Asp Gln Ser Phe Phe Asp Ser Thr Met Glu Phe Ser
            180                 185                 190

Ser Val Ser Leu Leu Asn Glu Leu Phe Gln Lys Gly Thr Val Ser Arg
        195                 200                 205

Pro Lys Tyr Thr Val Arg Leu Ala Pro Ser Gly Asp Ile Ser Trp Glu
    210                 215                 220

Thr Thr Leu His Leu Thr Phe His Glu Asp Asn Ser Thr Arg Ser Ile
225                 230                 235                 240

Thr Thr Val Gly Val Gly Arg Thr Lys Ser Glu Ser Lys Glu Gly Ala
                245                 250                 255

Ser Phe Asn Ala Leu Lys Ile Ile Gly Lys Val Pro Ala Val Phe Leu
            260                 265                 270

Asn Gly Arg Lys Lys Asp Ser Ala Glu Ile Thr Gly Val Asn Gln Ser
```

```
                275                 280                 285
Asp Leu Asn Val Cys Arg Phe Cys Gly Asn Tyr Tyr
                290                 295                 300
```

*NYLANDERIA FULVA* VIRUS

CROSS REFERENCE TO RELATED APPLICATIONS

This application claims priority to U.S. Patent Application 61/762,529 filed Feb. 8, 2013.

BACKGROUND OF THE INVENTION

1. Field of the Invention

This invention relates to a novel virus that infect *Nylanderia fulva*. The invention also relates to polynucleotide sequences of this novel virus, to biopesticides containing this novel virus, and methods of using the biopesticides.

2. Description of the Prior Art

*Nylanderia fulva* (Mayr), previously *Paratrechina pubens* (see, Gotzek, et al., PLoS ONE 7(9):e45314 (2012); LaPolla, et al., *Syst. Entomol.* 35:118-131 (2010)), is an invasive ant species that in recent years has developed into a serious pest problem in the Caribbean and United States (see, e.g., Wetterer and Keularts, *Entomol.* 91:423-427 (2008); and MacGown and Layton, *Midsouth Entomol.* 3:44-47 (2010)). A rapidly expanding range, explosive localized population growth, and control difficulties have elevated this ant to pest status. Professional entomologists and the pest control industry in the United States are urgently trying to understand its biology and develop effective control methods (see, e.g., Drees, et al., College Station: Texas A&M. 129-134 p. (2009) (insects.tamu.edu/fireant/research/projects/pdf/rasberrycrazyant.pdf); Warner and Scheffrahn, Gainesville: University of Florida, (2010) (edis.ifas.ufl.edu/pdffiles/IN/IN56000.pdf); Calibeo and Oi, ENY-2006 (IN889) ed. Gainesville: University of Florida (2011) (edis.ifas.ufl.edu/pdffiles/IN/IN88900.pdf)). Efforts have primarily focused on pursuing development of insecticide-based control strategies (Meyers, College Station: Texas A&M. 163 p. (2008) (urbanentomology.tamu.edu/pdf/meyer_dissertation.pdf)), as well as the effort to identify self-sustaining, biological control agents specific to *N. fulva*. While viruses can be important biological control agents against pest insect populations (Lacey, et al., *Biol. Cont.* 21:230-248 (2001)), none are known to infect *N. fulva*.

There remains a need for biocontrol agents and/or biopesticides that eliminate or at least reduce the spread of *N. fulva* and their colonies. The present invention is directed to a novel *N. fulva* virus, polynucleotides of the novel virus, biopesticides containing the novel *N. fulva* virus, and methods of using the biopesticides to control the *N. fulva* population in an area.

BRIEF DESCRIPTION OF THE INVENTION

It is an object of this invention to have at least one novel virus that infects *Nylanderia fulva* and other types of crazy ants.

It is an object of this invention to have a biopesticide containing at least one novel virus that infects *Nylanderia fulva* and other types of crazy ants.

It is another object of this invention to have a biopesticide containing at least one novel virus that infects *Nylanderia fulva* and other types of crazy ants. It is a further object of this invention that the biopesticide contains a carrier. The carrier can be a liquid or solid. It is another object of this invention that the carrier be a food source for the crazy ants.

It is an object of this invention to have a novel cDNA sequence having the sequence set forth in SEQ ID NO: 93; or that has at least 95% identity to SEQ ID NO: 93; or that has at least 90% identity to SEQ ID NO: 93; or that has at least 85% identity to SEQ ID NO: 93.

It is an object of this invention to have a novel cDNA sequence having the sequence set forth in SEQ ID NO: 93; or that has at least 95% identity to SEQ ID NO: 93; or that has at least 90% identity to SEQ ID NO: 93; or that has at least 85% identity to SEQ ID NO: 93. It is a further object of this invention to have the RNA equivalent of these sequences, or the RNA equivalent of the reverse complement of these sequences and which are viral genomic sequences. It is another object of this invention that the virus having these sequences infects crazy ants.

It is another object of this invention to have a novel virus that infects crazy ants and contains genomic RNA, the genomic RNA being the RNA equivalent of SEQ ID NO: 93; the RNA equivalent of the reverse complement of SEQ ID NO: 93; or a sequence that has at least 95%, 90% or 85% identity to these sequences. It is a further object of this invention to have a biopesticide containing this novel virus and, optionally, a carrier. It is another object of this invention that the carrier is optionally a food source for crazy ants, or optional a substance that eases distribution of the biopesticide. The carrier can be optionally a liquid, gel or a solid. It is another object of this invention to have a method of reducing the population of crazy ants in a colony or eradicating a colony of crazy ants by spreading this biopesticide in areas around a crazy ant colony or in areas where the crazy ants feed.

It is an object of this invention to have a novel polyprotein that is encoded by the novel cDNA sequence contained in SEQ ID NO: 93; the complement of SEQ ID NO: 93; or the reverse complement of SEQ ID NO: 93; or a sequence that has at least 95%, 90% or 85% identity to these sequences.

It is an object of this invention to have a novel virus that contains RNA which encodes a novel polyprotein that is encoded by the novel cDNA sequence contained in SEQ ID NO: 93; the complement of SEQ ID NO: 93; or the reverse complement of SEQ ID NO: 93; or a sequence that has at least 95%, 90% or 85% identity to these sequences. It is a further object of the invention that the novel virus which encodes this novel polyprotein infects crazy ants. It is another object of this invention to have a biopesticide containing this novel virus. The biopesticide can optionally contain a carrier. The carrier can be a solid, gel or a liquid. Optionally the carrier is a food source for crazy ants, or optional a substance that eases distribution of the biopesticide. It is another object of this invention to have a method of reducing the population of crazy ants in a colony or eradicating a colony of crazy ants by spreading this biopesticide in areas around a crazy ant colony or in areas where the crazy ants feed.

It is an object of this invention to have a polyprotein encoded by the amino acid sequence of SEQ ID NO: 94; or a sequence that has at least 95%, 90% or 85% identity to SEQ ID NO: 94. It is another object of this invention to have a novel virus that contains RNA which encodes the novel polyprotein having the amino acid sequence of SEQ ID NO: 94, or a sequence that has at least 95%, 90% or 85% identity to SEQ ID NO: 94. It is a further object of this invention that the novel virus infects crazy ants. It is another object of this invention to have a biopesticide containing this novel virus. The biopesticide can optionally contain a carrier. The carrier can be optionally a solid, gel or a liquid. Optionally the carrier is a food source for crazy ants, or optional a substance that eases distribution of the biopesticide. It is another object of this invention to have a method of reducing the population of crazy ants in a colony or eradicating a colony of crazy ants by spreading this biopesticide in areas around a crazy ant colony or in areas where the crazy ants feed.

It is an object of this invention to have a polyprotein containing at least one amino acid sequence selected from SEQ ID NOs: 95, 96, and 97; or a sequence that has at least 95%, 90% or 85% identity to SEQ ID NOs: 95, 96, and 97. It is another object of this invention to have a novel virus that contains RNA which encodes the novel polyprotein having at least one amino acid sequence selected from SEQ ID NOs: 95, 96, and 97; or a sequence that has at least 95%, 90% or 85% identity to SEQ ID NOs: 95, 96, and 97. It is a further object of this invention that the novel virus infects crazy ants. It is another object of this invention to have a biopesticide containing this novel virus. The biopesticide can optionally contain a carrier. The carrier can be optionally a solid, gel or a liquid. Optionally the carrier is a food source for crazy ants, or optional a substance that eases distribution of the biopesticide. It is another object of this invention to have a method of reducing the population of crazy ants in a colony or eradicating a colony of crazy ants by spreading this biopesticide in areas around a crazy ant colony or in areas where the crazy ants feed.

It is an object of this invention to have a novel virus that can be identified by containing genomic RNA, the cDNA of which can hybridize to a primer having a sequence set forth in SEQ ID NOs: 11-88 and mixtures thereof. It is further object of this invention that this novel virus infects crazy ants. It is another object of this invention to have a biopesticide containing this novel virus that infects crazy ants which contains genomic RNA, the cDNA of which can hybridize to a primer having a sequence set forth in SEQ ID NOs: 11-88 and mixtures thereof. It is also an object of this invention that the biopesticide sickens and/or kills crazy ants. It is a further object of this invention that the biopesticide contains a carrier where the carrier can be a food of crazy ants or a substance that eases distribution or application of the biopesticide. It is another object of this invention that the carrier be either a solid, gel or a liquid. It is another object of this invention to have a method of reducing the population of crazy ants in a colony or eradicating a colony of crazy ants by spreading this biopesticide in areas around a crazy ant colony or in areas where the crazy ants feed.

DETAILED DESCRIPTION OF THE INVENTION

*N. fulva* is a species of ants formerly called *Paratrechina pubens* and is commonly called "crazy ants". Crazy ants can include tawny crazy ants, brown crazy ants, hairy crazy ants, Caribbean crazy ants, and Rasberry crazy ants. Any hybrid ants that are infected by the virus of this invention are included in the term "crazy ants". Crazy ants are an invasive species that are a serious pest in the Caribbean and United States. Chemical pesticides may kill crazy ants but can also kill other beneficial or desired insects and animals. To date, no virus or bacteria has been identified which infects crazy ants and which can be used as a biopesticide against crazy ants. This invention identifies at least one virus that infects *N. fulva*, NfV, and can be used as a biopesticide against crazy ants.

A "biocontrol agent" or "biopesticide" are interchangeable terms and are broadly defined as a composition containing a protein, glycoprotein, polysaccharide, lipid, or other substance produced by animals, plants, bacteria, viruses, phages, fungi, protozoa, etc., that, when a pest ingests, touches, or otherwise comes in contact with the composition, exerts a deleterious effect on the pest. Such deleterious effect can include, but is not limited to, inhibiting reproduction and/or killing the pest. Viruses, bacteria, phages, protozoa, fungi, etc., can be biocontrol agents or biopesticides in that these organisms can infect the pest, injure, and/or kill the pest. Further, some animals are biocontrol agents or biopesticides, such as endoparasitic wasps. In this invention, the at least one virus described herein, NfV, can be a biocontrol agent or biopesticide for the crazy ants.

A biopesticide can optionally include a carrier component which can be a liquid or a solid material. The carrier usually is an inert agent that does not repel the pest. The carrier may assist in the delivery of the biocontrol agent that targets the pest. The carrier may be a food source for crazy ants. A carrier can be a liquid or gel, such as, but not limited to, water, sugar water, saline solution, oil, or any other liquid or gel that does not adversely affect the viability and/or activity of the biocontrol organism or compound. A solid carrier can be, for example, the pest's food or a substance that assists with the application or distribution of the biocontrol agent. For crazy ants, non-limiting examples of solid carriers include corn cob grits, extruded corn pellets, boiled egg yolks, and frozen insects such as crickets.

Optionally, a chemical pesticide, insecticide, or synergists can be included in the biopesticide. Non-limiting examples of pesticides, insecticides, or synergists for this invention include, abamectin, dinotefuran, avermectins, chlorfenapyr, indoxacarb, metaflumizone, imidacloprid, fipronil, hydramethylon, sulfluramid, hexaflumuron, pyriproxyfen, methoprene, lufenuron, dimilin, chlorpyrifos, neem, azadiractin, boric acid, their active derivatives, and the like. These pesticides/insecticides act as stressor which may be required to initiate replication of the biocontrol organism which, in turn, results in death of the pests.

An "effective amount" or "amount effective for" is the minimum amount of a biocontrol agent to affect the desired effect on the organism targeted by the biocontrol agent. For this invention, an "effective amount" or "amount effective for" is the minimum amount of the virus(es) or composition containing the virus(es) needed to cause the death of crazy ants. An effective amount of the virus(es) of this invention will infect and kill a sufficient number of crazy ants such that the colony is reduced in size as compared to a similar colony that is not treated, or such that the colony collapses completely thereby eradicating the crazy ants. The precise amount needed may vary in accordance with the particular virus used, the other components of the biopesticide, the colony being treated, the environment in which the colony is located, and the environment before, during, and after application of the biocontrol agent. The exact amount of virus needed per dose of biopesticide and/or the amount of biopesticide needed can be easily determined by one of ordinary skill in the art using the teachings presented herein.

The present invention includes the method of using the virus(es) of the present invention to reduce or eradicate a population of crazy ants. These methods involve spreading, distributing, or administrating the virus(es) of the present invention or the biopesticide of the present invention to crazy ants, their colonies, areas around their colonies, and/or areas where the crazy ants forage and obtain food. The amount of biopesticide used is an effective amount for killing crazy ants, reducing the size of the colony compared to an untreated colony, or eradicating the crazy ants and their colony.

The terms "isolated", "purified", or "biologically pure" as used herein, refer to material that is substantially or essentially free from components that normally accompany the material in its native state. In an exemplary embodiment, purity and homogeneity are determined using analytical chemistry techniques such as polyacrylamide gel electrophoresis or high performance liquid chromatography. A nucleic acid that is the predominant species present in a preparation is substantially purified. In an exemplary embodiment, the term "purified" denotes that a nucleic acid or protein gives rise to essentially one band in an electrophoretic gel. An isolated or purified virus is a virus that is separated from other viruses with which it is found in nature or from the virus' host. Typically, isolated nucleic acids or proteins or viruses have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyino sine residues (see e.g., Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98(1994)).

In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide.

As used herein a nucleic acid "probe", oligonucleotide "probe", or simply a "probe" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. Probes may contain a label so that one can determine if the probe is bound to the target sequence. By assaying for the presence or absence of the probe, one can detect the presence or absence of the select sequence or subsequence. A probe can be bound, either covalently, through a linker or a chemical bond, or noncovalently, through ionic, van der Waals, electrostatic, or hydrogen bonds, to a label such that the presence of the probe may be detected by detecting the presence of the label bound to the probe. In other exemplary embodiments, probes are indirectly labeled e.g., with biotin to which a streptavidin complex may later bind.

The term "label" as used herein, refers to a composition detectable by spectroscopic, photochemical, biochemical, immunochemical, or chemical means. Exemplary labels include $^{32}P$, fluorescent dyes, electron-dense reagents, enzymes (e.g., as commonly used in an ELISA), biotin, digoxigenin, or haptens and proteins for which antisera or monoclonal antibodies are available. In one exemplary embodiment, labels can be isotopes, chromophores, luminphores, chromogens, etc. Labels can also involve two or more compounds, only one of which need be attached to the probe. An example of a pair of compounds that are labels is biotin and streptavidin, where biotin is attached to the probe and later reacts with streptavidin which is added after the probe binds the target sequence.

The term "primer" as used herein, refers to short nucleic acids, typically a DNA oligonucleotide of at least about 15 nucleotides in length. In an exemplary embodiment, primers are annealed to a complementary target DNA or RNA strand by nucleic acid hybridization to form a hybrid between the primer and the target DNA or RNA strand. Annealed primers are then extended along the target strand by a DNA polymerase enzyme or reverse transcriptase. Primer pairs can be used for amplification of a nucleic acid sequence, e.g., by the polymerase chain reaction (PCR) or other nucleic-acid amplification methods known in the art.

PCR primer pairs are typically derived from a known sequence, for example, by using computer programs intended for that purpose such as Primer (Version 0.5 ©1991, Whitehead Institute for Biomedical Research, Cambridge, Mass.). One of ordinary skill in the art will appreciate that the specificity of a particular probe or primer increases with its length. Thus, for example, a primer comprising 20 consecutive nucleotides of a promoter complex sequence will anneal to a related target sequence with a higher specificity than a corresponding primer of only 15 nucleotides. Thus, in an exemplary embodiment, greater specificity of a nucleic acid primer or probe is attained with probes and primers selected to comprise 20, 25, 30, 35, 40, 50 or more consecutive nucleotides of a selected sequence.

Nucleic acid probes and primers are readily prepared based on the nucleic acid sequences disclosed herein. Methods for preparing and using probes and primers and for labeling and guidance in the choice of labels appropriate for various purposes are discussed, e.g., in Green and Sambrook, *Molecular Cloning, A Laboratory Manual* 4th ed. 2012, Cold Spring Harbor Laboratory; and Ausubel et al., eds., *Current Protocols in Molecular Biology,* 1994—current, John Wiley & Sons). The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant or wild-type) form of the cell or express native genes that are otherwise abnormally expressed, over expressed, under expressed or not expressed at all.

The following terms are used to describe the sequence relationships between two or more nucleic acids or polynucleotides: "reference sequence", "comparison window", "sequence identity", "percentage of sequence identity", and "substantial identity". A reference sequence is a defined sequence used as a basis for a sequence comparison; a reference sequence may be a subset of a larger sequence, or gene sequence given in a sequence listing.

The terms "identical" or percent "identity", in the context of two or more nucleic acids or polypeptide sequences, refer to two or more sequences or subsequences that are the same or have a specified percentage of amino acid residues or nucleotides that are the same (e.g., 85% identity, 90% identity, 99%, or 100% identity), when compared and aligned for maximum correspondence over a comparison window, or designated region as measured using a sequence comparison algorithm or by manual alignment and visual inspection.

The phrase "substantially identical", in the context of two nucleic acids or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, the substantial identity exists over a region of the sequences that is at least about 50 residues in length. In another exemplary embodiment, the substantial identity exists over a region of the sequences that is at least about 100 residues in length. In still another exemplary embodiment, the substantial identity exists over a region of the sequences that is at least about 150 residues or more, in length. In one exemplary embodiment, the sequences are substantially identical over the entire length of nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from about 20 to about 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., eds., *Current Protocols in Molecular Biology*, 1995 supplement).

An exemplary algorithm for sequence comparison is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984)).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=4, and a comparison of both strands.

The BLAST algorithm also performs a statistical analysis of the similarity between two sequences (see, e.g., Karlin and Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively hybridizes to" or "specifically hybridizes to" refers to the binding, duplexing, or hybridizing of a molecule only to a particular nucleotide sequence under stringent hybridization conditions when that sequence is present in a complex mixture (e.g., total cellular or library DNA or RNA). In general, two nucleic acid sequences are said to be "substantially identical" when the two molecules or their complements selectively or specifically hybridize to each other under stringent conditions.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Hybridization with Nucleic Probes Parts I and II*, Elsevier (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, SxSSC and 1% SDS incubated at 42° C. or SxSSC and 1% SDS incubated at 65 ° C., with a wash in 0.2×SSC and 0.1% SDS at 65° C. However, other high stringency hybridization conditions known in the art can be used.

Nucleic acids that do not hybridize to each other under stringent conditions are still substantially identical if the polypeptides that they encode are substantially identical. This situation can occur, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981). Using of machines for sequencing DNA or RNA is known in the art field.

This invention utilizes routine techniques in the field of molecular biology. Basic texts disclosing the general methods of use in this invention include Green and Sambrook, 4th ed. 2012, Cold Spring Harbor Laboratory; Kriegler, *Gene Transfer and Expression: A Laboratory Manual* (1993); and Ausubel et al., eds., *Current Protocols in Molecular Biology*, 1994—current, John Wiley & Sons. Unless otherwise noted, technical terms are used according to conventional usage. Definitions of common terms in molecular biology maybe found in e.g., Benjamin Lewin, *Genes IX*, published by Oxford University Press, 2007 (ISBN 0763740632); Krebs, et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

For all examples described herein, unless otherwise stated, the crazy ants colonies are obtained from field sites located in Desoto (April, 2011), Hillsborough (April, 2011), Alachua (March through May, 2011), and Duval (March, 2011) counties in Florida and subsequently are maintained in the laboratory. Colonies are reared separately in nesting tubes as described by Oi and Williams, *Environ. Entomol.* 32:1171-1176 (2003). The colonies are fed frozen crickets, 10% sucrose solution, and water. Identifications of crazy ants are made based on characters listed in Trager (*Sociobiol.* 9:51-162 (1984)), LaPolla, et al. (Syst Entomol 35: 118-131 (2010)), and Gotzek, et al. (PloS ONE 7(9): e45314 10 p. (2012)). While there may possible be some uncertainty regarding species assignment of the crazy ants from Florida, Texas, Louisiana and Mississippi based on morphometric and DNA sequence data, all of these types of arts are considered crazy ants for the purpose of this invention. In addition, NfV has been confirmed present in *N. fulva* collected in Nassau County, Fla., and a different site in Alachua County, Fla., in 2013.

Having now generally described this invention, the same will be better understood by reference to certain specific examples and the accompanying drawings, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

EXAMPLE 1 cDNA Library Generation and Analysis

Total RNA is extracted from samples of the colonies of *N. fulva* using TRIzol® RNA isolation reagents (Life Technologies, Carlsbad, Calif.) according to the manufacturer's instructions. Samples are taken from nine colonies. A total of 609 ants of different life stages (workers, alates, queens, larvae, pupae, and eggs) are used to prepare the total RNA. RNA quality of each preparation is assessed by microfluidic analysis on an Agilent 2100 Bioanalyzer (Agilent, Cary, N.C.) using the RNA 6000 Nano kit (Agilent, Cary, N.C.) according to the manufacturer's directions. Microfluidic assays are completed immediately after RNA extraction using a 1 µl volume of purified sample. RNA samples of acceptable quality are pooled and are used as source material for mRNA purification. mRNA is isolated from the total RNA sample using the Oligotex mRNA Mini Kit (Qiagen, Valencia, Calif.) following the manufacturer's instructions. The isolated mRNA is then utilized to prepare a non-normalized fragment library suitable for 454 platform sequencing using the NEBNext mRNA Sample Pre Reagent Set 2 (New England BioLabs, Ipswich, Mass.) following the manufacturer's protocol. The library is used as a template for emulsion PCR using the GS Titanium LV emulsion PCR Kit (Lib-L; Roche, Basel, Switzerland) following the manufacturer's instructions. DNA beads generated from the emulsion PCR reactions are used for Titanium plate 454 sequencing, using the GS Titanium Sequencing Kit XLR70 (Roche, Basel, Switzerland). De novo assembly is performed for the generated sequencing data using the Newbler software (Roche).

The initial assembly of the sequences is performed with Newbler Assembler Version 2.3 (454 Life Science, Branford, Conn.), employing masking and trimming sequencing repeats, primers and/or adaptors used in cDNA library preparation. The hybridized sequences (contigs and leftover singletons) are further assembled with Paracel Transcript Assembler version 3.0.0 (PTA; Paracel Inc., Pasadena, Calif.).

In PTA, all sequences are masked for universal and species-specific vector sequences, adaptors, and PCR primers used in cDNA library creation. *Escherichia coli* contamination and mitochondrial and ribosomal RNA genes are identified and are removed from input sequences using default settings to ascertain the novelty of the sequences. The poly (A/T) tails and intrinsic repeats, such as simple sequence repeats and short interspersed elements (SINE), are annotated prior to clustering and assembly. Low base-call quality data are trimmed from the ends of individual sequences and sequences<75 by are excluded from consideration during initial pair-wise comparisons. After cleanup, sequences are passed to the PTA clustering module for pair-wise comparison and then to the CAP3-based PTA assembly module for assembly. The PTA assembly is performed based on the sequences of the contigs and the leftover singletons generated from the Newbler assembly.

The single production GS-FLX Titanium 454 platform sequencing run (two half plates) of the non-normalized *N. fulva* expression library generates 1,306,177 raw sequence reads comprising 450 Mbp. De novo assembly of the raw data with Newbler yields 22,044 contigs and 232,338 singletons. Subsequent assembly by PTA results in the generation of 59,017 non-redundant sequences, including 27,348 contigs (average size 794 bp) and 31,669 singlets (average size 295 bp). Among these sequences, 27.9% (16,458) are greater than 500 by and 72.1% (42,533) are greater than 300 bp. BLASTX analysis of these non-redundant nucleotide sequences identifies 25,898 (43.9%) nucleotide sequences with significant (e-value<$1e^4$) similarity, and 33,119 (56.1%) nucleotide sequences have no significant similarity. A significant percentage (47%) of the gene sequences (12,174) identified is found to be unique to *N. fulva*.

Large-scale homology database searches of the PTA sequence data set are conducted against the National Center for Biotechnology Information (NCBI) NR and NT databases using BLAST (blastx and blastn) with an in-house computational pipeline. To obtain a more accurate and complete description of potential gene function for each queried sequence, the top 100 BLAST hits are retrieved. Sequences with the best scoring BLAST hit ($\leq 1e^{-5}$) and the corresponding gene ontology (GO) classification are annotated to the queried sequence (Koski and Golding, *J. Molec. Evol.* 52:540-542 (2001)). GO term assignments are binned according to the categories, biological processes, cellular components, and molecular functions. BLAST results and GO term assignments are completed in BlastQuest, an SQL database developed by the Interdisciplinary Center for Biotechnology Research, University of Florida, that facilitates similarity-based sequence annotation with gene ontology information (Farmerie, et al., *Data Know Eng.* 53:75-97 (2005)). In addition, the sequences are characterized with respect to functionally annotated genes by BLAST searching against NCBI specific reference sequences (RefSeq) for *Homo sapiens* (38,556 sequences), *Drosophila* (21,099 sequences) and Formicidae (74,540 sequences). Queries are considered to have a clear homolog of the searched organism when e-values are<$1e^{-4}$, the length of the aligned segment is≥50 bp, and identity>85%, which essentially eliminates spurious hits while preventing elimination of medium-sized proteins.

Raw 454 reads and assembled contigs are deposited in the NCBI database. The *N. fulva* sequence data are publicly available and accessible through the NCBI website accession numbers Ant_454Assem_NCBI.sqn: JP773711 - JP820231.

EXAMPLE 2

Identification of Viral Sequences

Sequences identified as exhibiting significant viral homology/identity are selected and are further evaluated in an attempt to establish their origin, viral, host, or otherwise. Evaluations are also conducted to ascertain whether identified viral sequences are simply being ingested by the ants or are replicating (i.e., *N. fulva* is serving as host). BLAST analysis of the 59,017 non-redundant sequences yielded from the *N. fulva* library results in the identification of 51 sequences of putative viral origin. Among them, 31 sequences do not meet the threshold for significance (an expectation score>1e$^{-4}$) and are not examined further to establish their source; viral, host, or otherwise. However, despite expectation scores greater than 1e$^{-4}$, some of these sequences could represent a virus that infect *N. fulva*.

Twenty sequences from the *N. fulva* expression library yield significant BLAST expectation scores of putative viral origin; nine sequences are similar to DNA virus sequences and eleven to RNA virus sequences. Of the eleven sequences related to genes of RNA viruses, six negative-sense and five positive-sense, single-stranded RNA virus genes are identified. Three sequences of ostensibly positive-sense, single-stranded RNA virus(es) are examined in more detail.

EXAMPLE 3

Confirmation of Viral Sequences

To confirm that the suspected RNA virus sequences are actually from RNA viruses, the forward and reverse oligonucleotide primers listed in Table 1 are designed based on EST Assem.3776.C1 (GenBank Accession No. JP780688.1; SEQ ID NO: 1), EST Assem.13287.C1 (GenBank Accession No. JP790645.1; SEQ ID NO: 2), and EST Assem.8702.C1 (GenBank Accession No. JP786492.1; SEQ ID NO: 3).

TABLE 1

| EST Designation | Forward oligo-nucleotide primer name, sequence (5'→3'), and SEQ ID NO. | Reverse oligo-nucleotide primer name, sequence (5'→3'), and SEQ ID NO. |
| --- | --- | --- |
| Assem.3776.C1 SEQ ID NO: 1 | p1167 CCCTACTGACTGACGAAC AGATTGCTTC SEQ ID NO: 4 | p1168 TGTTGTTGAGCGTAATGA GTCCGTCCT SEQ ID NO: 5 |
| Assem.13287.C1 SEQ ID NO: 2 | p1169 ACTTCACTTGTATATGGA GATCCCTCCATACAA SEQ ID NO: 6 | p1170 TTGCTTCGTGATATGTCA TTCCTGGATACAAT SEQ ID NO: 7 |
| Assem.8702.C1 SEQ ID NO: 3 | p1172 TGGTACTGGTATGTCGGA TGTGATGAGCT SEQ ID NO: 8 | p1171 TGAGGTCTTGACACTGGT AGTGTTGAAATGA SEQ ID NO: 9 |

PCR is conducted with RNase-treated DNA extracted from the same *N. fulva* colonies used in expression library creation in Example 1. No amplicon is generated indicating that the sequences are not *N. fulva* genomic sequences. Next, mRNA is isolated from *N. fulva* colonies as per the protocol in Example 1 and the primers in Table 1 are used to generate amplicons using RT-PCR. Two-step RT-PCR is employed to amplify a portion of the genome strand. First, 1 µl (50 ng) of total RNA is mixed with 10 mM dNTPs and 1 µm of the appropriate tagged oligonucleotide primer, is heated to 65° C. for 5 minutes, and then is placed on ice for at least 1 minute. First strand buffer and Superscript reverse transcriptase (RT, Invitrogen, Carlsbad, Calif.) are then added, and the reaction mixture is incubated at 55° C. for 1 hour before inactivating the RT at 70° C. for 15 minutes. Unincorporated oligonucleotides are digested with 10 units of Exonuclease I (New England Biolabs, Ipswich, Mass.) at 37° C. for 1 hour. The reaction is terminated by heating to 80° C. for 20 minutes. Amplification is observed in approximately 50% to approximately 66% of the samples, thus it is assumed that the sequences are not host (or other) origin, because viral infections rarely exhibit an incidence of 100% among field-collected arthropods (Fuxa and Tanada, *Epizootiology of insect diseases*. New York: John Wiley and Sons. (1987)).

Next, tagged-RT-PCR is conducted with the above indicated primers to detect the replicating genomic strand (see Craggs, et al., *J. Virol. Methods* 94:111-120 (2001)). This method permits discrimination of each genome strand without carryover effects causing false positive detection of either strand. Tagged-RT-PCR employs the use of the appropriate oligonucleotide primer in Table 1 appended at the 5' end with a TAG sequence (5'-GGCCGTCATGGTGGCGAATAA-3'; SEQ ID NO: 10) that is used in a cDNA-synthesis reaction (forward primer for positive-strand viruses and reverse primer for negative-strand viruses).

PCR is subsequently conducted in a 25 µl volume containing 2 mM MgCl$_2$, 200 µM dNTP mix, 0.5 units of Platinum Taq DNA polymerase (Invitrogen, Carlsbad, Calif.), 0.2 µM of each oligonucleotide primer, and 5 µl of the cDNA preparation. PCR is conducted with the following temperature regime, 94° C. for 2 minutes followed by 35 cycles of 94° C. for 15 seconds, 56-60° C. for 15 seconds; 68° C. for 30 seconds and a final 68° C. step for 5 minutes in a thermal cycler. PCR products are separated on a 1% agarose gel and are visualized by SYBR-safe (Invitrogen, Carlsbad, Calif.) staining. The replicating strand for each of these ESTs are detected by tagged-PCR which indicates that *N. fulva* is a host for the virus. Next, the amplicon is cloned by ligating into the pCR4 expression vector and transforming the pCR4 expression vector into TOP10 competent cells (Invitrogen, Carlsbad, Calif.). Its sequence is verified by Sanger sequencing which is performed by the University of Florida, Interdisciplinary Center for Biotechnology Research (Gainesville, Fla.). Thus, EST Assem.3776.C1, EST Assem.13287.C1, and EST Assem.8702.C1 are considered to be from at least one virus infecting *N. fulva*.

The sequences of Assem.13287.C1, Assem.8702.C1, and Assem.3776.C1 exhibit some homology to unclassified positive-strand RNA viruses. Specifically, Assem.13287.C1 exhibits some homology with the helicase region (ATPase chaperone functionality) of Kelp fly virus (Hartley, et al., *J. Virol.* 79:13385-13398 (2005)), and Assem.8702.C1 exhibits some homology with the 3C-like protease region of polyprotein 1 (5'-proximal ORF) of *Solenopsis invicta* virus 3 (SINV-3) (Valles and Hashimoto, *Virology* 388:354-361 (2009)). Assem3776.C1 also exhibits some homology with SINV-3 at the interface of the 3C-protease and RNA-dependent RNA polymerase. The replicative form of the genome (minus or negative strand) is detected in a small percentage of field-collected *N. fulva* providing strong evidence that these sequences correspond to positive-strand RNA viruses that infect *N. fulva*. All of these sequences exhibit identity to viruses that infect arthropods (Diptera and Hymenoptera). Thus, detection of Assem.13287.C1, Assem.8702.C1, and Assem.3776.C1 by tagged-RT-PCR among a small percentage of field-collected *N. fulva* colonies suggests that these sequences are of viral origin and appear to replicate in *N. fulva*. Sanger sequencing of these amplicons verifies their identity.

The primers listed in Table 1 (SEQ ID NOs: 4, 5, 6, 7, 8, and 9) can be used to identify NfV. The reverse primers (SEQ ID NOs: 5, 7, and 9) can hybridize to the RNA genome of NfV and to a cDNA of the viral genome. The forward primers (SEQ ID NOs: 4, 6, and 8) hybridize to a negative RNA strand of the viral genome and to a cDNA of the viral genome. NfV, as a positive-strand RNA virus, contains only the positive strand, single-strand RNA in its capsid. But during active replication in infected cells, the infected cells contain copies of both the positive-strand RNA and the negative-strand RNA which serves as template to make additional copies of the positive-strand RNA.

EXAMPLE 4

Characteristics of Virus

The virus of this invention, referred to as Nylanderia fulva virus or NfV represents the first virus to be discovered from an ant in the Formicine. The virus of this invention possesses features consistent with placement within the order *Picornavirales:* 1. non-enveloped particles with a diameter around 30 nm, 2. a positive-sense, single-stranded RNA genome, 3. no production of subgenomic RNA, and 4. a polyprotein containing helicase, protease, and RNA-dependent RNA polymerase (RdRp) domains (Le Gall, et al., *Archives of Virology* 153, 715-27 (2008)).

A series of 5' RACE reactions are conducted to obtain the upstream sequences of the genome of the virus(es) of this invention using the 5' RACE system (Invitrogen, Carlsbad, Calif.) and primer walking. For each reaction, cDNA is synthesized for 50 minutes at 48° C. with 2.5 µg of total RNA extracted with TRIzol® RNA isolation reagents (Life Technologies, Carlsbad, Calif.) according to manufacturer's instructions from Nylanderia fulva virus or Nylanderia fulva virus-infected ants with gene-specific oligonucleotide primer, the RNA template is degraded with RNase H, and the cDNA purified. The 3' end of the cDNA is polycytidylated with terminal deoxynucleotidyl transferase and dCTP. The tailed cDNA is then amplified with a nested GSP (3' end) and an abridged anchor primer (AAP). Gel-purified amplicons are ligated into the pCR4-TOPO vector, transformed into TOP10 competent cells (Invitrogen, Carlsbad, Calif.) and are sequenced by the Interdisciplinary Center for Biotechnology Research (University of Florida).

To obtain sequences downstream of the amplicon, 3' RACE reactions are conducted with the GeneRacer kit (Invitrogen, Carlsbad, Calif.) according to manufacturer's instructions. cDNA is synthesized from total RNA (1 µg) using the GeneRacer appended Oligo dT primer. The cDNA is amplified by PCR with a GSP and GeneRacer 3' primer. Amplicons are cloned and sequenced as described for 5' RACE. Table 2 contains the sequences of the GSP primers, as well as the sequences of other primers where were purchased from Invitrogen (AUAP, AAP, 3' primer, and oligo dT primer) (Carlsbad, Calif.).

The GSP primers listed in Table 2 (SEQ ID NOs: 11-88) can be used to identify NfV. The reverse primers (SEQ ID NOs: 11-16, 18-20, 22, 24, 25, 27-31, 33, 35, 40, 42-44, 46, 49-54, 56-59, 62, 64-68, 72, and 75-85) can hybridize to the RNA genome of NfV and to a cDNA of the viral genome. The forward primers (SEQ ID NOs: 17, 21, 23, 26, 32, 34, 36-39, 41, 45, 47, 48, 55, 60, 61, 63, 69-71, 73, 74, 86, 87, and 88) hybridize to a negative RNA strand of the viral genome and to a cDNA of the viral genome. NfV, as a positive strand, single-strand RNA virus, contains only the positive strand RNA in its capsid. But during active replication in infected cells, the infected cells contain copies of both the positive-strand RNA and the negative-strand RNA which serves as template to make additional copies of the positive-strand RNA.

TABLE 2

| Primer name/ Orientation | Sequence |
| --- | --- |
| p1230/R | GAAGCAATCTGTTCGTCAGTCAGTAGGGT (SEQ ID NO: 11) |
| p1231/R | TGTCATTTTCCATAGGTAGTTTCGTAGGCAGT (SEQ ID NO: 12) |
| p1232/R | TCCGTCACTATCCTTCAACAAATCAAACCA (SEQ ID NO: 13) |
| p1236/R | AATTCTTGTGTAGCCTTGAGTTGTTGAAATTGA (SEQ ID NO: 14) |
| p1237/R | TTCTCAAACAAATTACCTGAGACGTTCTGAGT (SEQ ID NO: 15) |
| p1238/R | ACCTTTTCCTTGACAGCTACCGCACGT (SEQ ID NO: 16) |
| P1267/F | AGCATGGTATTGAATTTATAGCTCATGAAGAAT (SEQ ID NO: 17) |
| P1268/R | ATTCTTCATGAGCTATAAATTCAATACCATGCT (SEQ ID NO: 18) |
| P1269/R | AATCAGGAAATTGGATTACTTGATCTTTTGGAATGT (SEQ ID NO: 19) |
| p1270/R | GTATTCAAATTCATTAAGTTTCCAAAGGTAATTTCATGT (SEQ ID NO: 20) |
| p1271/F | CAATTCTATCTTATTTCCACTTCACTAAGAGC (SEQ ID NO: 21) |
| p1272/R | GCTCTTAGTGAAGTGGAAATAAGATAGAATTG (SEQ ID NO: 22) |
| p1273/F | TCCTCAATGGGAGAAGTGTTGTGCTT (SEQ ID NO: 23) |
| p1278/R | TCGCACCATTCATCTTTATATATGATAACGC (SEQ ID NO: 24) |
| p1279/R | ATGCCTTCTGGCTCATTTATAACTGCGCCA (SEQ ID NO: 25) |
| p1280/F | AGCATTGAGATTCCCGATTCAGCCGACTT (SEQ ID NO: 26) |
| p1281/R | AAGTCGGCTGAATCGGGAATCTCAATGCT (SEQ ID NO: 27) |
| p1282/R | AATCGAGATTTATAAGTTCCTCTTTCCTCCTAACA (SEQ ID NO: 28) |
| p1283/R | AAGAGCCAATATAGCAAATTTGCCAAGATGAGGA (SEQ ID NO: 29) |
| p1290/R | TCTTAGTGAAGTGGAAATAAGATAGAATTGTTTCCT (SEQ ID NO: 30) |
| p1291/R | ACGTTTATAATCTATGGCAAATACGTGATCGAAT (SEQ ID NO: 31) |
| p1292/F | ACTGCCTACGAAACTACCTATGGAAAATGACA (SEQ ID NO: 32) |
| p1303/R | GTCTTGTCAAACGTTTATAATCTATGGCAAATACGTGA (SEQ ID NO: 33) |
| p1304/F | TCACGTATTTGCCATAGATTATAAACGTTTGACAAGAC (SEQ ID NO: 34) |

TABLE 2-continued

| Primer name/Orientation | Sequence |
|---|---|
| p1305/R | TCAGCTCCACAAACATGTCATGAAAATTCGCATAGG (SEQ ID NO: 35) |
| p1306/F | CCTATGCGAATTTTCATGACATGTTTGTGGAGCTGA (SEQ ID NO: 36) |
| p1307/F | TATGCGTGTTGAGACTTGCCTGCTCTGGCA (SEQ ID NO: 37) |
| p1308/F | ATGAATTTGAATACAACTAATCAAACCTTTTTCGACA (SEQ ID NO: 38) |
| p1309/F | ACAGGCTATCATGGGCCCTGGTACA (SEQ ID NO: 39) |
| p1318/R | AGCCACTTCATGTATTGTTTATAGATCATGTCCTT (SEQ ID NO: 40) |
| p1319/F | AAGGACATGATCTATAAACAATACATGAAGTGGCT (SEQ ID NO: 41) |
| p1320/R | GGTTCATATACTACCAAATAGTCCTTCCGACTATC (SEQ ID NO: 42) |
| p1321/R | GTTATAAACAGTTTCCATGGTGCATCACACTTATC (SEQ ID NO: 43) |
| p1322/R | ACGGGACTTGACAAATATTCCATAATTAACTGCCT (SEQ ID NO: 44) |
| p1323/F | AGGCAGTTAATTATGGAATATTTGTCAAGTCCCGT (SEQ ID NO: 45) |
| p1324/R | TCCTGAGAAACTTCATCAAAGAAGTTCAGGTCTGGT (SEQ ID NO: 46) |
| p1325/F | ACCAGACCTGAACTTCTTTGATGAAGTTTCTCAGGA (SEQ ID NO: 47) |
| p1330/F | TGTTAGGTCGCTCTCTTCTTTGATAGATGCATCTT (SEQ ID NO: 48) |
| p1331/R | AAGATGCATCTATCAAAGAAGAGAGCGACCTAACA (SEQ ID NO: 49) |
| p1332/R | AGATTTATGCTGCATGCAGGCAATTTGGGT (SEQ ID NO: 50) |
| p1333/R | TCCAGTTCCAGTGAACAGAACTGCTACAGGTTCCT (SEQ ID NO: 51) |
| p1334/R | TTGTAAGCCAAGTTCATCAACGCCTGAGTCT (SEQ ID NO: 52) |
| p1335/R | AAGAAGGTTTGGTTGGTTGTATTCAGGTTCAT (SEQ ID NO: 53) |
| p1336/R | TACCCTGCTGCTAGTTGTGTACCAGGGCCCAT (SEQ ID NO: 54) |
| p1337/F | AAGGGTAACGTTCCCAACAAGGGTGAGCAAT (SEQ ID NO: 55) |
| p1338/R | ATTGCTCACCCTTGTTGGGAACGTTACCCTT (SEQ ID NO: 56) |
| p1339/R | CAATCTGTCGTAGTGGGATCAATGTTCGTACCGT (SEQ ID NO: 57) |
| p1340/R | ATTGAATCACTCTGGTTGACTCCTTCAACTGGCT (SEQ ID NO: 58) |
| p1341/R | AAGAGCACCAAGCACAACACTTCTCCCATTGAGGA (SEQ ID NO: 59) |
| p1342/F | TCCTCAATGGGAGAAGTGTTGTGCTTGGTGCTCTT (SEQ ID NO: 60) |
| p1343/F | AACTTAAACCTTTCGACACTTGGGAAGAAGTA (SEQ ID NO: 61) |
| p1344/R | AGCGAAGGAGTTGGTGAACAATGGCGA (SEQ ID NO: 62) |
| p1353/F | AGAATGTTCTCGACCCAGTTTACGGTTG (SEQ ID NO: 63) |
| p1354/R | CAACCGTAAACTGGGTCGAGAACATTCT (SEQ ID NO: 64) |
| p1355/R | ACTCGGACACTCCCTGATCTGAATTTCTGGA (SEQ ID NO: 65) |
| p1356/R | ACTTTCTCGACCATCTCTACATTAGTACGCA (SEQ ID NO: 66) |
| p1364/R | AGTGTAGGCCATCTATTCTCTTTTGTCAGT (SEQ ID NO: 67) |
| p1365/R | TAGGGACATAGTCAATTTCCATCGCAAGG (SEQ ID NO: 68) |
| p1366/F | ACTAAGAGCCTTGAGCCACAGCACCTATCTTCATT (SEQ ID NO: 69) |
| p1367/F | TCTTAAGAAGGAAACAATTCTATCTTACTTCCACT (SEQ ID NO: 70) |
| p1368/F | ACTACGACAGATTGGGCCGAAGCAGCAAAT (SEQ ID NO: 71) |
| p1369/R | TGCTGCTCCTTTACACATATCAAAGAAGGTT (SEQ ID NO: 72) |
| p1370/F | TCAACAGAACCTTTTCTCATGTACCAAAATCA (SEQ ID NO: 73) |
| p1383/F | ATGTTCTCGACCCAGTTTACGGTTGGCGGT (SEQ ID NO: 74) |
| p1384/R | TTGTGGTTCAACCACTTTCTCGACCATCTCTACA (SEQ ID NO: 75) |
| p1385/R | TGGAATAGCATTGACACAAATGATATAATCGCAGA (SEQ ID NO: 76) |
| p1386/R | TCATCAACCTTTTCATCAGTCAACAATTCGGA (SEQ ID NO: 77) |
| p1387/R | ATCTACTACAAGCTGTGCCTCATTTACTGAAGGA (SEQ ID NO: 78) |
| p1388/R | AAGAAGGGACGGAGGGTCGCCGTTGAA (SEQ ID NO: 79) |
| p1389/R | TGTAGGCCATCTATTCTCTTTTGTCAGTTTAGTA (SEQ ID NO: 80) |
| p1390/R | ACTCAAGCTTCAAATTCTGGCACCAGGTCTGGA (SEQ ID NO: 81) |
| p1391/R | ATTACACGTGTATGTGTATGTGTGTGTAT (SEQ ID NO: 82) |
| p1392/R | ACATTGCAAAATAATGTTTATTTATCAAGGATAATAT (SEQ ID NO: 83) |
| p1393/R | ACGACGTTATTACGTTCTTATCGGCATATTTACT (SEQ ID NO: 84) |
| p1394/R | TATAGACATCGTATTTCGTTTGCTTACTATCA (SEQ ID NO: 85) |

TABLE 2-continued

| Primer name/Orientation | Sequence |
|---|---|
| p1395/F | TACTAAACTGACAAAAGAGAATAGATGGCCTACA (SEQ ID NO: 86) |
| p1396/F | TGAAATTAAAGACTTTCCTCGCCTTGCGATGGA (SEQ ID NO: 87) |
| p1397/F | TGGGAGGACTTGACTATTCCTATACGTGACGGA (SEQ ID NO: 88) |
| AUAP | GGCCACGCGTCGACTAGTAC (SEQ ID NO: 89) |
| AAP | GGCCASGCGTCGACTAGTACGGGIIGGGIIGGGIIG (SEQ ID NO: 90) |
| 3' Primer | GCTGTCAACGATACGCTACGTAACG (SEQ ID NO: 91) |
| Oligo dT primer | GCTGTCAACGATACGCTACGTAACGGCATGACAGT G(T)$_{24}$ (SEQ ID NO: 92) |

R = reverse
F = forward

The cloning and sequencing described above, using the primers in Table 2, resulted in a DNA sequence of approximately 80% of the NfV's genome (SEQ ID NO: 93). Of course, the viral sequence, being RNA, will contain uracil bases instead of the indicated thymidine bases. Analysis of this genomic sequence reveals an amino acid sequence of a putative polypeptide of 2634 amino acids with a molecular weight of 300863 daltons (SEQ ID NO: 94). Within the polypeptide exist the following domains: RNA helicase domain from amino acid 501-751 (SEQ ID NO: 95); NTP binding protein from amino acid 2000-2200 (SEQ ID NO: 96); and RNA-dependent RNA polymerase (RdRp) from amino acid 2251-2550 (SEQ ID NO: 97).

EXAMPLE 5

Viral Transmission

To evaluate the transmission of the virus of this invention, uninfected crazy ant nests are identified by RT-PCR as per Example 1, excavated from the field, and parsed into equivalent colonies. Colonies are infected by a modification of the method described by Ackey and Beck (*J. Insect Physiol.* 18:1901-1914 (1972)). Briefly, approximately 1 to approximately 5 grams of crazy ants from a colony infected with the virus of this invention are homogenized in a Waring blender with either 30 ml of 10% sucrose prepared with deionized water or 30 ml of refined soybean oil for 1 minute at high speed. The homogenates are filtered through three layers of cheesecloth and then filtered by vacuum in a Buchner funnel through a number 1 Whatman paper. The 10% sucrose-virus bait is used in this form. The oil-virus bait preparation is mixed with pregel defatted corn grit (Illinois Cereal Mills, Paris, Ill.) at 30% oil-virus by weight to adsorb the oil onto the corn grit. In addition, approximately 1 to approximately 5 grams of infected crazy ants are mixed with 21 g of freeze-killed adult house crickets. The mixture is pulverized with a mortar and pestle to create a crude paste. These three types of infected food sources are placed in a position that the uninfected crazy ant colony will find it and partake thereof. The control colony is provided the same three food sources, but without the infected crazy ants added to it. Crazy ants from the treated and untreated colonies are sampled at about 3, 11 and 18 days after introduction of the food source (infected or non-infected) and analyzed for the presence of the virus of this invention by RT-PCR using the primers in Table 1 or Table 2 and the protocol described above.

EXAMPLE 6

Biopesticide Efficacy

To evaluate the efficacy of using the virus of this invention as a biopesticide, non-infected colonies are obtained and placed in the laboratory. Homogenates of crazy ant colonies infected with the virus of this invention are used as sources of virus for preparation of the bait formulations. Aliquots are blended in a Waring blender with either 30 ml of 10% sucrose prepared with deionized water or 30 ml of refined soybean oil for 1 minute at high speed. The homogenates are filtered through three layers of cheesecloth and then filtered by vacuum in a Buchner funnel through a number 1 Whatman paper. The 10% sucrose-virus bait is used in this form. The oil-virus bait preparation is mixed with pregel defatted corn grit (Illinois Cereal Mills, Paris, Ill.) at 30% oil-virus by weight to adsorb the oil onto the corn grit. The third aliquot of infected crazy ants is mixed with 21 g of freeze-killed adult house crickets. The mixture is pulverized with a mortar and pestle to create a crude paste. Virus content of each bait formulation is determined by quantitative PCR using the primers in Table 1 or Table 2.

Test colonies (n=10/treatment) are transferred into clean trays without food two days before test treatments and then pulse exposed to virus bait formulations for 24 hours. Control colonies receive access to crickets, sugar water, and oil on corn grits, all without the virus homogenate. The baits are subsequently placed on the floor of the ant rearing tray. Treatment and control colonies are randomly distributed in the holding trays until virus replication was confirmed in the treatments, after which, colonies positive for virus replication are removed into separate holding trays in an adjacent rack to limit chances for contamination of uninfected colonies.

Bait-treated and control colonies are periodically evaluated to ascertain their relative health by monitoring the ratio of brood to workers. Colonies are assigned a score of 4 if they are rapidly growing with brood mass greater than worker mass. A score of 3 indicates a healthy growing colony with brood mass approximately 70% of worker mass. A score of 2 indicates a colony in poor health with brood mass of approximately 50% of worker mass. A score of 1 indicates a sick colony with brood mass approximately 25% of worker mass. A score of 0 is reserved for colonies without any brood. During evaluations each nest tube is manually checked and intermediate scores are assigned as appropriate. Control colonies are always checked first and gloves were changed between each colony to avoid mechanically transmitting the virus. Each colony is evaluated to determine the quantity of workers (g) and brood (g), worker and larval mortality (number of dead workers counted in the housing tray), the queen weight, queen ovary rating, the number of eggs laid by the queen in a 24 hour period.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference.

We, the inventors, claim:

1. A method of reducing the population of crazy ants in a colony or eradicating a colony of crazy ants comprising applying, in an amount effective to kill crazy ants, a biopesticide to areas around a crazy ant colony or to areas where the crazy ants feed, wherein said biopesticide comprises a virus that infects and kills crazy ants and a carrier, wherein said virus comprises a polynucleotide having a sequence which encodes an RNA-dependent RNA polymerase having the amino acid sequence of SEQ ID NO: 97.

2. The method of claim 1 wherein said carrier comprises a food source for crazy ants.

3. The method of claim 2 wherein said food source is selected from the group consisting of corn grits, extruded corn pellets, boiled egg yolks, dead insects, and a combination thereof.

4. The method of claim 1 wherein said carrier is selected from the group consisting of water, sugar water, saline solution, and oil.

5. A method of reducing the population of crazy ants in a colony or eradicating a colony of crazy ants comprising applying, in an amount effective to kill crazy ants, a biopesticide to areas around a crazy ant colony or to areas where the crazy ants feed, wherein said biopesticide comprises a virus that infects and kills crazy ants and a carrier, wherein said virus comprises a polynucleotide having a sequence which encodes an RNA-dependent RNA polymerase having an amino acid sequence selected from the group consisting of an amino acid sequence that is at least 95% identical to amino acids 1-300 of SEQ ID NO: 97, an amino acid sequence that is at least 90% identical to amino acids 1-300 of SEQ ID NO: 97, and an amino acid sequence that is at least 85% identical to amino acids 1-300 of SEQ ID NO: 97, and wherein said encoded RNA-dependent RNA polymerase has RNA-dependent RNA polymerase activity.

6. The method of claim 5 wherein said carrier comprises a food source for crazy ants.

7. The method of claim 6 wherein said food source is selected from the group consisting of corn grits, extruded corn pellets, boiled egg yolks, dead insects, and a combination thereof.

8. The method of claim 5 wherein said carrier is selected from the group consisting of water, sugar water, saline solution, and oil.

* * * * *